(12) United States Patent
Vitolo et al.

(10) Patent No.: US 7,946,960 B2
(45) Date of Patent: May 24, 2011

(54) SYSTEM AND METHOD FOR PREDICTING ATHLETIC ABILITY

(75) Inventors: Corrine Vitolo, Westford, MA (US); Larry Scannell, Westford, MA (US)

(73) Assignee: SmartSports, Inc., Westford, MA (US)

( * ) Notice: Subject to any disclaimer, the term of this patent is extended or adjusted under 35 U.S.C. 154(b) by 0 days.

(21) Appl. No.: 11/709,914

(22) Filed: Feb. 22, 2007

(65) Prior Publication Data

US 2008/0188353 A1 Aug. 7, 2008

Related U.S. Application Data

(63) Continuation-in-part of application No. 11/702,424, filed on Feb. 5, 2007, now abandoned.

(51) Int. Cl.
*A63B 71/00* (2006.01)
*G06F 19/00* (2011.01)
(52) U.S. Cl. ............. 482/8; 482/1; 700/91; 700/93
(58) Field of Classification Search ............ 482/1–9; 434/219, 257–258, 249; 473/151, 453, 199, 473/452, 192; 700/91–93; 463/1; 600/587, 600/595
See application file for complete search history.

(56) References Cited

U.S. PATENT DOCUMENTS

| | | | |
|---|---|---|---|
| 4,029,315 A | 6/1977 | Bon | |
| 4,070,018 A | 1/1978 | Hodges | |
| 4,309,032 A | 1/1982 | Facius | |
| 4,461,477 A | 7/1984 | Stewart | |
| 4,563,005 A | 1/1986 | Hand et al. | |
| 4,577,863 A | 3/1986 | Ito et al. | |
| 4,759,219 A | 7/1988 | Cobb et al. | |
| 4,858,922 A | 8/1989 | Santavaci | |
| 4,870,868 A | 10/1989 | Gastgeb et al. | |
| 4,915,384 A | 4/1990 | Bear | |
| 5,056,783 A | 10/1991 | Matcovich et al. | |
| 5,221,082 A | 6/1993 | Curchod | |
| 5,249,967 A | 10/1993 | O'Leary et al. | |
| 5,257,084 A | 10/1993 | Marsh | |
| 5,437,457 A * | 8/1995 | Curchod | 473/199 |
| 5,700,204 A | 12/1997 | Teder | |
| 5,798,519 A | 8/1998 | Vock et al. | |
| 5,868,578 A * | 2/1999 | Baum | 434/247 |

(Continued)

FOREIGN PATENT DOCUMENTS

GB 2294403 A 5/1996

(Continued)

OTHER PUBLICATIONS

Worldseries.com, "Latest Technology Enhances Playoffs" www.mlb.mlb.com printed Oct. 19, 2006, 3 pages.

(Continued)

*Primary Examiner* — Loan Thanh
*Assistant Examiner* — Sundhara M Ganesan
(74) *Attorney, Agent, or Firm* — Wolf, Greenfield & Sacks, P.C.

(57) ABSTRACT

A system for predicting athletic ability is disclosed. The system includes at least one device for measuring at least a first athletic parameter and a second athletic parameter, and a computer for calculating a performance score based upon the first athletic parameter and the second athletic parameter. The performance score is predictive of athletic ability. Methods of predicting athletic ability based upon a plurality of athletic parameters are also disclosed.

21 Claims, 34 Drawing Sheets

U.S. PATENT DOCUMENTS

| | | | |
|---|---|---|---|
| 5,980,429 | A | 11/1999 | Nashner |
| 5,988,861 | A | 11/1999 | Baum |
| 6,042,492 | A * | 3/2000 | Baum ........................... 473/453 |
| 6,073,489 | A | 6/2000 | French et al. |
| 6,093,923 | A | 7/2000 | Vock et al. |
| 6,098,458 | A * | 8/2000 | French et al. .............. 73/379.04 |
| 6,190,287 | B1 | 2/2001 | Nashner |
| 6,204,813 | B1 | 3/2001 | Wadell et al. |
| 6,224,387 | B1 | 5/2001 | Jones |
| 6,292,130 | B1 | 9/2001 | Cavallaro et al. |
| 6,293,802 | B1 | 9/2001 | Ahlgren |
| 6,304,665 | B1 | 10/2001 | Cavallaro et al. |
| 6,308,565 | B1 | 10/2001 | French et al. |
| 6,320,173 | B1 | 11/2001 | Vock et al. |
| 6,371,871 | B1 | 4/2002 | Rappaport et al. |
| 6,390,934 | B1 | 5/2002 | Winfield et al. |
| 6,396,041 | B1 | 5/2002 | Vock et al. |
| 6,430,997 | B1 | 8/2002 | French et al. |
| 6,431,990 | B1 | 8/2002 | Manwaring |
| 6,456,232 | B1 | 9/2002 | Milnes et al. |
| 6,513,018 | B1 * | 1/2003 | Culhane ........................... 705/35 |
| 6,517,353 | B1 | 2/2003 | Jones |
| 6,561,917 | B2 | 5/2003 | Manwaring |
| 6,632,158 | B1 | 10/2003 | Nashner |
| 6,634,967 | B2 | 10/2003 | Daniel |
| 6,640,200 | B1 | 10/2003 | Baum |
| 6,671,390 | B1 | 12/2003 | Barbour et al. |
| 6,702,292 | B2 | 3/2004 | Takowsky |
| 6,709,351 | B2 | 3/2004 | Hori |
| 6,765,726 | B2 | 7/2004 | French et al. |
| 6,774,349 | B2 | 8/2004 | Vock et al. |
| 6,784,826 | B2 | 8/2004 | Kane et al. |
| 6,786,730 | B2 | 9/2004 | Bleckley et al. |
| 6,876,496 | B2 | 4/2005 | French et al. |
| 6,881,067 | B2 | 4/2005 | Tarry |
| 6,921,268 | B2 * | 7/2005 | Bruno et al. ................... 434/323 |
| 6,968,243 | B1 * | 11/2005 | Oh .................................. 700/91 |
| 6,981,876 | B2 | 1/2006 | Bleckley et al. |
| 7,021,140 | B2 | 4/2006 | Perkins |
| 7,038,855 | B2 | 5/2006 | French et al. |
| 2003/0044757 | A1 * | 3/2003 | Tarry et al. ..................... 434/257 |
| 2003/0149613 | A1 * | 8/2003 | Cohen et al. ..................... 705/11 |
| 2003/0190592 | A1 * | 10/2003 | Bruno et al. ................... 434/322 |
| 2003/0207718 | A1 | 11/2003 | Perlmutter |
| 2004/0127337 | A1 | 7/2004 | Nashner |
| 2004/0152058 | A1 * | 8/2004 | Browne et al. ................ 434/258 |
| 2005/0012023 | A1 * | 1/2005 | Vock et al. ................... 250/206.1 |
| 2005/0032582 | A1 * | 2/2005 | Mahajan et al. .............. 473/222 |
| 2005/0143198 | A1 | 6/2005 | Charge |
| 2005/0202907 | A1 * | 9/2005 | Otten et al. ................... 473/457 |
| 2005/0215340 | A1 * | 9/2005 | Stites et al. ................... 473/233 |
| 2005/0288119 | A1 | 12/2005 | Wang et al. |
| 2006/0008116 | A1 * | 1/2006 | Kiraly et al. ................... 382/103 |
| 2006/0068927 | A1 | 3/2006 | Rankin et al. |
| 2006/0073449 | A1 | 4/2006 | Kumar et al. |

FOREIGN PATENT DOCUMENTS

| | | |
|---|---|---|
| WO | WO 01/21266 A1 | 3/2001 |
| WO | WO 01/41884 A1 | 6/2001 |
| WO | WO 02/39363 A1 | 5/2002 |
| WO | WO 2005/119272 A1 | 12/2005 |

OTHER PUBLICATIONS

All Stars Scouting "Recruitment Advice" www.webball.com printed Jul. 24, 2006, 8 pages.

All Stars Scouting "Recruitment Advice, Scouts Ranking Scale" www.webball.com printed Jul. 14, 2006, 1 page.

CSwing "Professional Affordable Golf Swing Analysis Software" www.cswing.com printed Aug. 1, 2006, 3 pages.

CCM Marketing "SeeSwing Launches the World's First All-In-One Golf Swing Performance Unit in conjunction with its Online Performance Academy" www.golfbusinesswire.com printed Aug. 2, 2006, 2 pages.

* cited by examiner

Pitching

FIG. 5A(1)

Fastball

| Scale | Accuracy % | (MPH) | Movement Inches (4 Seam) | Score (4 Seam) | Movement Inches (2 Seam) | Score 2 Seam | Movement Inches (Cut) | Score Cut |
|---|---|---|---|---|---|---|---|---|
| 80 | 90+ | 98+ | 6+ | 194+ | 9+ | 197+ | 13+ | 201+ |
| 70 | 85 | 93-97 | 5-5.9 | 183-193 | 8-8.9 | 186-196 | 12-12.9 | 190-200 |
| 60 | 80 | 90-92 | 4-4.9 | 174-182 | 7-7.9 | 177-185 | 11-11.9 | 181-189 |
| 50 | 75 | 88-89 | 3-3.9 | 161-173 | 6-6.9 | 164-176 | 10-10.9 | 168-180 |
| 40 | 70 | 85-87 | 2-2.9 | 157-160 | 5-5.9 | 160-163 | 9-9.9 | 154-167 |
| 30 | 65 | 83-84 | 1-1.9 | 149-156 | 4-4.9 | 152-159 | 8-8.9 | 156-163 |
| 20 | 60- | 82- | 0.9- | 148- | 5.0- | 151- | 7.9- | 155- |

Curve Ball

| (MPH) | Movement (Inches) | Score Curve |
|---|---|---|
| 85+ | 25+ | 200+ |
| 82-84 | 22-23.9 | 189-199 |
| 80-82 | 19-21.9 | 179-188 |
| 77-79 | 16-18.9 | 169-178 |
| 74-76 | 13-15.9 | 159-168 |
| 71-73 | 11-12.9 | 149-158 |
| 70- | 10.9- | 148- |

FIG. 5A(2)

Slider

| Scale | Accuracy % | (MPH) | Break Angle (Degrees) | Score |
|---|---|---|---|---|
| 80 | 90+ | 92+ | 60+ | 242+ |
| 70 | 85 | 88-92 | 50-59 | 223-241 |
| 60 | 80 | 85-87 | 40-49 | 205-222 |
| 50 | 75 | 83-84 | 30-39 | 188-204 |
| 40 | 70 | 80-82 | 20-29 | 170-187 |
| 30 | 65 | 77-79 | 10-19 | 152-169 |
| 20 | 60- | 76- | 9- | 151- |

Change Up

| Fastball Differential | Movement (Inches) | Score |
|---|---|---|
| 20+ | 24.0+ | 44+ |
| 16-18 | 21-23.9 | 37-43 |
| 13-15 | 18-20.9 | 31-36 |
| 10-12 | 15-17.9 | 25-30 |
| 7-9 | 12-14.9 | 19-24 |
| 4-8 | 9-11.9 | 13-18 |
| 3- | 8.9- | 12- |

Splitter

| (MPH) | Movement (Inches) | Score Split |
|---|---|---|
| 88+ | 20+ | 108+ |
| 85-87 | 18-19.9 | 103-107.9 |
| 83-84 | 16-17.9 | 99-102.9 |
| 80-82 | 14-15.9 | 94-98.9 |
| 77-79 | 12-13.9 | 89-93.9 |
| 75-76 | 10-11.9 | 85-88.9 |
| | | |

Pitching

Fastball

| Scale | MPH | Movement Inches (4 Seam) | Score (4 Seam) | Movement Inches (2 Seam) | Score 2 Seam | Movement Inches (Cut) |
|---|---|---|---|---|---|---|
| 80 | 98+ | 6+ | 104+ | 9+ | 107+ | 13+ |
| 70 | 93-97 | 5-5.9 | 98-103 | 8-8.9 | 101-106 | 12-12.9 |
| 60 | 90-92 | 4-4.9 | 94-97 | 7-7.9 | 97-100 | 11-11.9 |
| 50 | 88-89 | 3-3.9 | 91-93 | 6-6.9 | 94-96 | 10-10.9 |
| 40 | 85-87 | 2-2.9 | 87-90 | 5-5.9 | 90-93 | 9-9.9 |
| 30 | 83-84 | 1-1.9 | 84-86 | 4-4.9 | 87-89 | 8-8.9 |
| 20 | 82- | 0.9- | 83- | 5.0- | 86- | 7.9- |

Curve

| Scale | MPH | Movement (Inches) | Score |
|---|---|---|---|
| 80 | 85+ | 24+ | 109+ |
| 70 | 82-84 | 22-23.9 | 104-108.9 |
| 60 | 80-81 | 19-21.9 | 99-103.9 |
| 50 | 77-79 | 16-18.9 | 93-98.9 |
| 40 | 74-76 | 13-15.9 | 87-92.9 |
| 30 | 71-73 | 11-12.9 | 82-86.9 |
| 20 | 70- | 10.9- | 81.9 |

Slider

| Scale | MPH | Break Angle (Degrees) | Score |
|---|---|---|---|
| 80 | 92+ | 60+ | 152+ |
| 70 | 88-91 | 50-59 | 138-151 |
| 60 | 85-87 | 40-49 | 125-137 |
| 50 | 83-84 | 30-39 | 113-124 |
| 40 | 80-82 | 20-29 | 100-112 |
| 30 | 77-79 | 10-19 | 87-99 |
| 20 | 76- | 9- | 86- |

FIG.5A(3)

Fastball

| Scale | MPH | Fastball Differential | Movement Inches | Score | Separation to Release | Tempo | Deceptive Visibility Factor (Seconds) | Score |
|---|---|---|---|---|---|---|---|---|
| 80 | 98+ | 20+ | 24.0+ | 44+ | 3.5+ | 3.5+ | 3.5+ | 10.5+ |
| 70 | 93-97 | 16-18 | 21-23.9 | 37-43 | 3.2-3.4 | 3.2-3.4 | 3.2-3.4 | 9.6-10.4 |
| 60 | 90-92 | 13-15 | 18-20.9 | 31-36 | 2.0-3.1 | 2.9-3.1 | 2.9-3.1 | 8.7-9.5 |
| 50 | 88-89 | 10-12 | 15-17.9 | 25-30 | 2.5-2.8 | 2.5-2.8 | 2.5-2.8 | 7.5-8.6 |
| 40 | 85-87 | 7-9 | 12-14.9 | 19-24 | 2.2-2.4 | 2.2-2.4 | 2.2-2.4 | 6.6-7.4 |
| 30 | 83-84 | 4-8 | 9-11.9 | 13-18 | 1.9-2.1 | 1.9-2.1 | 1.9-2.1 | 5.7-6.5 |
| 20 | 82- | 3- | 8.9- | 12- | 1.8- | 1.8- | 1.8- | 5.6- |

Splitter

| Scale | MPH | Accuracy % | Score | Scale | MPH | Movement Inches | Score Cut |
|---|---|---|---|---|---|---|---|
| 80 | 98+ | 90+ | 188+ | 80 | 88+ | 20+ | 108+ |
| 70 | 93-97 | 85 | 178-187 | 70 | 85-87 | 18-19.9 | 103-107 |
| 60 | 90-92 | 80 | 170-177 | 60 | 83-84 | 16-17.9 | 99-102 |
| 50 | 88-89 | 75 | 163-169 | 50 | 80-82 | 14-15.9 | 94-98 |
| 40 | 85-87 | 70 | 155-162 | 40 | 77-79 | 12-13.9 | 89-93 |
| 30 | 83-84 | 65 | 148-154 | 30 | 75-76 | 10-11.9 | 85-88 |
| 20 | 82- | 60- | 147- | 20 | 74- | 9.9- | 84- |

FIG. 5B(2)

Fastball

| Scale | Accuracy % | Movement Inches (4 Seam) | Movement Inches (2 Seam) | Movement Inches (Cut) | Score 4 Seam | Score 2 Seam | Score Cut |
|---|---|---|---|---|---|---|---|
| 80 | 90+ | 6+ | 9+ | 13+ | 96+ | 99+ | 103+ |
| 70 | 85 | 5-5.9 | 8-8.9 | 12-12.9 | 90-95 | 93-98 | 97-102 |
| 60 | 80 | 4-4.9 | 7-7.9 | 11-11.9 | 84-89 | 87-82 | 91-96 |
| 50 | 75 | 3-3.9 | 6-6.9 | 10-10.9 | 78-83 | 81-86 | 85-90 |
| 40 | 70 | 2-2.9 | 5-5.9 | 9-9.9 | 72-77 | 75-80 | 79-84 |
| 30 | 65 | 1-1.9 | 4-4.9 | 8-8.9 | 66-71 | 69-74 | 73-78 |
| 20 | 60- | 0.9- | 5.0- | 7.9- | 65- | 68- | 72- |

FIG. 5B(4)

| Scale | Accuracy % | Splitter | |
|---|---|---|---|
| | | Movement Inches | Score |
| 80 | 90+ | 20+ | 110+ |
| 70 | 85 | 18-19.9 | 103-109 |
| 60 | 80 | 16-17.9 | 96-102 |
| 50 | 75 | 14-15.9 | 89-95 |
| 40 | 70 | 12-13.9 | 82-88 |
| 30 | 65 | 10-11.9 | 75-81 |
| 20 | 60- | 9.9 - | 74 - |

FIG. 5B(6)

| Scale | Separation to Release | Deceptive Visibility Factor (Seconds) | Score |
|---|---|---|---|
| 80 | 3.5+ | 3.5+ | 7+ |
| 70 | 3.2-3.4 | 3.2-3.4 | 6.4-6.9 |
| 60 | 2.9-3.1 | 2.9-3.1 | 5.8-6.3 |
| 50 | 2.5-2.8 | 2.5-2.8 | 5-5.7 |
| 40 | 2.2-2.4 | 2.2-2.4 | 4.4-4.9 |
| 30 | 1.9-2.1 | 1.9-2.1 | 3.8-4.3 |
| 20 | 1.8 - | 1.8 - | 3.7 - |

FIG. 5B(3)

| Scale | Accuracy % | Curve | |
|---|---|---|---|
| | | Movement Inches | Score |
| 80 | 90+ | 25+ | 115+ |
| 70 | 85 | 22-23.9 | 107-114 |
| 60 | 80 | 19-21.9 | 99-106 |
| 50 | 75 | 16-18.9 | 91-98 |
| 40 | 70 | 13-15.9 | 83-90 |
| 30 | 65 | 11-12.9 | 76-82 |
| 20 | 60- | 10.9 - | 75 - |

FIG. 5B(5)

| Scale | Accuracy % | Slider | |
|---|---|---|---|
| | | Break Angle (Degrees) | Score |
| 80 | 90+ | 60+ | 150+ |
| 70 | 85 | 50-59 | 135-149 |
| 60 | 80 | 40-49 | 120-134 |
| 50 | 75 | 30-39 | 105-119 |
| 40 | 70 | 20-29 | 90-104 |
| 30 | 65 | 10-19 | 75-89 |
| 20 | 60- | 9 - | 72 - |

FIG. 5B(7)

| Scale | Accuracy % | Change-Up | | Score |
|---|---|---|---|---|
| | | Fastball Differential | Movement Inches | |
| 80 | 90+ | 20+ | 24.0+ | 44+ |
| 70 | 85 | 16-18 | 21-23.9 | 37-43 |
| 60 | 80 | 13-15 | 18-20.9 | 31-36 |
| 50 | 75 | 10-12 | 15-17.9 | 25-30 |
| 40 | 70 | 7-9 | 12-14.9 | 19-24 |
| 30 | 65 | 4-8 | 9-11.9 | 13-18 |
| 20 | 60- | 3- | 8.9- | 12- |

FIG. 5B(8)

| Scale | Tempo Time | Deceptive Visibility Factor (Seconds) | Score |
|---|---|---|---|
| 80 | 3.5+ | 3.5+ | 7+ |
| 70 | 3.2-3.4 | 3.2-3.4 | 6.4-6.9 |
| 60 | 2.9-3.1 | 2.9-3.1 | 5.8-6.3 |
| 50 | 2.5-2.8 | 2.5-2.8 | 5-5.7 |
| 40 | 2.2-2.4 | 2.2-2.4 | 4.4-4.9 |
| 30 | 1.9-2.1 | 1.9-2.1 | 3.8-4.3 |
| 20 | 1.8- | 1.8- | 3.7- |

Hitting

FIG. 6A(1)

| Scale | Bat Speed (MPH) | Distance (Feet) | Ball Velocity Off Bat (MPH) | Barrel Accuracy % | Barrel Angle at Contact % | Score |
|---|---|---|---|---|---|---|
| 80 | 95+ | 425+ | 125+ | 98+ | 98+ | 841+ |
| 70 | 90-94 | 400-425 | 115-125 | 95-97 | 95-97 | 795-840 |
| 60 | 85-89 | 375-400 | 105-115 | 92-94 | 92-94 | 749-794 |
| 50 | 80-84 | 350-375 | 95-105 | 89-91 | 89-91 | 703-748 |
| 40 | 75-79 | 325-350 | 85-95 | 86-88 | 86-88 | 657-702 |
| 30 | 70-74 | 300-325 | 75-85 | 83-85 | 83-85 | 611-656 |
| 20 | 70 - | 300 - | 75 - | 82 - | 82 - | 610 - |

FIG. 6A(2)

| Scale | Bat Speed (MPH) | Barrel Accuracy % | Score | Scale | Bat Speed (MPH) | Throwing Accuracy % | Score |
|---|---|---|---|---|---|---|---|
| 80 | 95+ | 98+ | 193-195 | 80 | 95+ | 95+ | 190+ |
| 70 | 90-94 | 95-97 | 185-192 | 70 | 90-94 | 90 | 180-189 |
| 60 | 85-89 | 92-94 | 177-184 | 60 | 85-89 | 85 | 170-179 |
| 50 | 80-84 | 89-91 | 169-176 | 50 | 80-84 | 80 | 160-169 |
| 40 | 75-79 | 86-88 | 161-168 | 40 | 75-79 | 75 | 150-159 |
| 30 | 70-74 | 83-85 | 153-160 | 30 | 70-74 | 70 | 140-149 |
| 20 | 70 - | 82 - | 152 - | 20 | 70 - | 65 - | 139 - |

FIG. 6A(3)

| Scale | Bat Speed (MPH) | Distance (Feet) | Score | Scale | Bat Speed (MPH) | Ball Velocity Off Bat (MPH) | Score | Scale | Bat Speed (MPH) | Barrel Angle at Contact % | Score |
|---|---|---|---|---|---|---|---|---|---|---|---|
| 80 | 95+ | 425+ | 520+ | 80 | 95+ | 125+ | 220 | 80 | 95+ | 98+ | 193-195 |
| 70 | 90-94 | 400-424 | 490-518 | 70 | 90-94 | 115-125 | 205-219 | 70 | 90-94 | 95-97 | 185-192 |
| 60 | 85-89 | 375-399 | 460-489 | 60 | 85-89 | 105-114 | 190-204 | 60 | 85-89 | 92-94 | 177-184 |
| 50 | 80-84 | 350-374 | 430-459 | 50 | 80-84 | 95-104 | 175-189 | 50 | 80-84 | 89-91 | 169-176 |
| 40 | 75-79 | 325-349 | 400-429 | 40 | 75-79 | 85-94 | 160-174 | 40 | 75-79 | 86-88 | 161-168 |
| 30 | 70-74 | 300-324 | 370-399 | 30 | 70-74 | 75-84 | 145-159 | 30 | 70-74 | 83-85 | 153-160 |
| 20 | 69 - | 299 - | 368 - | 20 | 70 - | 74 - | 144 - | 20 | 70 - | 82 - | 152 - |

FIG. 6A(4)

| Scale | Bat Speed (MPH) | Arm Strength (MPH) | Score | Scale | Bat Speed (MPH) | Glove to Release Time (Timed) | Score | Scale | Bat Speed (MPH) | Range (Left) | Range (Right) | Score | Scale | Distance (Feet) | Barrel Angle at Contact % | Score |
|---|---|---|---|---|---|---|---|---|---|---|---|---|---|---|---|---|
| 80 | 95+ | 90+ | 185+ | 80 | 95+ | .349- | 175+ | 80 | 95+ | 1.03- | 1.03- | 523+ | 80 | 425+ | 98+ | 523+ |
| 70 | 90-94 | 87-89 | 177-184 | 70 | 90-94 | .35-.399 | 160-174 | 70 | 90-94 | 1.3025-1.0525 | 1.3025-1.0525 | 495-522 | 70 | 400-424 | 95-97 | 459-522 |
| 60 | 85-89 | 83-86 | 168-176 | 60 | 85-89 | .40-.499 | 145-159 | 60 | 85-89 | 1.055-1.075 | 1.055-1.075 | 467-494 | 60 | 375-399 | 92-94 | 467-494 |
| 50 | 80-84 | 79-82 | 159-167 | 50 | 80-84 | .50-.599 | 130-144 | 50 | 80-84 | 1.0775-1.0975 | 1.0775-1.0975 | 439-466 | 50 | 350-374 | 89-91 | 439-466 |
| 40 | 75-79 | 76-79 | 151-158 | 40 | 75-79 | .60-.699 | 115-129 | 40 | 75-79 | 1.10-1.1225 | 1.10-1.1225 | 411-438 | 40 | 325-349 | 86-88 | 411-438 |
| 30 | 70-74 | 72-75 | 142-150 | 30 | 70-74 | .70-.799 | 100-114 | 30 | 70-74 | 1.125-1.1475 | 1.125-1.1475 | 383-410 | 30 | 300-324 | 83-85 | 383-410 |
| 20 | 70- | 71- | 141- | 20 | 70- | .80+ | 99- | 20 | 70- | 1.25+ | 1.25+ | 382- | 20 | 300- | 82- | 382- |

FIG. 6B(1)

| Scale | Distance (Feet) | Ball Velocity Off Bat (MPH) | Score | Scale | Distance (Feet) | Barrel Accuracy % | Score | Scale | Distance (Feet) | Arm Strength (MPH) | Score | Scale | Distance (Feet) | Throwing Accuracy % | Score |
|---|---|---|---|---|---|---|---|---|---|---|---|---|---|---|---|
| 80 | 425+ | 125+ | 550+ | 80 | 425+ | 98+ | 523+ | 80 | 425+ | 90+ | 515+ | 80 | 425+ | 95+ | 515+ |
| 70 | 400-425 | 115-124 | 515-549 | 70 | 400-424 | 95-97 | 495-522 | 70 | 400-424 | 87-89 | 487-514 | 70 | 400-424 | 90 | 487-514 |
| 60 | 375-400 | 105-114 | 480-514 | 60 | 375-399 | 92-94 | 467-494 | 60 | 375-399 | 83-86 | 458-486 | 60 | 375-399 | 85 | 458-486 |
| 50 | 350-375 | 95-104 | 445-479 | 50 | 350-374 | 89-91 | 439-466 | 50 | 350-374 | 79-82 | 429-457 | 50 | 350-374 | 80 | 429-457 |
| 40 | 325-350 | 85-94 | 410-444 | 40 | 325-349 | 86-88 | 411-438 | 40 | 325-349 | 75-78 | 400-428 | 40 | 325-349 | 75 | 400-428 |
| 30 | 300-325 | 75-84 | 375-409 | 30 | 300-324 | 83-85 | 383-410 | 30 | 300-324 | 72-77 | 372-399 | 30 | 300-324 | 70 | 372-399 |
| 20 | 300- | 74- | 374- | 20 | 300- | 82- | 382- | 20 | 299- | 70- | 371- | 20 | 299- | 65- | 371- |

FIG. 6B(1)

| Scale | Distance (Feet) | Glove to Release (Timed) | Score | Scale | Ball Velocity Off Bat (MPH) | Barrel Accuracy % | Score |
|---|---|---|---|---|---|---|---|
| 80 | 425+ | .299- | 505+ | 80 | 125+ | 98+ | 223-325 |
| 70 | 400-425 | .30-.399 | 470-504 | 70 | 115-124 | 95-97 | 210-222 |
| 60 | 375-400 | .40-.499 | 435-469 | 60 | 104-114 | 92-94 | 197-209 |
| 50 | 350-375 | .50-.599 | 400-434 | 50 | 95-104 | 89-91 | 184-196 |
| 40 | 325-350 | .60-.699 | 365-399 | 40 | 85-94 | 86-88 | 171-183 |
| 30 | 300-325 | .70-.799 | 330-364 | 30 | 75-84 | 83-85 | 156-170 |
| 20 | 300 - | .80+ | 329 - | 20 | 74 - | 82 - | 157 - |

FIG. 6B(2)

| Scale | Ball Velocity Off Bat (MPH) | Arm Strength (MPH) | Score |
|---|---|---|---|
| 80 | 125+ | 90+ | 215+ |
| 70 | 115-124 | 87-89 | 202-214 |
| 60 | 105-114 | 83-86 | 188-201 |
| 50 | 95-104 | 79-82 | 174-187 |
| 40 | 85-94 | 75-78 | 160-173 |
| 30 | 75-84 | 74-77 | 149-159 |
| 20 | 74 - | 70 - | 148 - |

FIG. 6B(3)

| Scale | Ball Velocity Off Bat (MPH) | Barrel Accuracy % | Score |
|---|---|---|---|
| 80 | 125+ | 98+ | 223-325 |
| 70 | 115-124 | 95-97 | 210-222 |
| 60 | 105-114 | 92-94 | 197-209 |
| 50 | 95-104 | 89-91 | 184-196 |
| 40 | 85-94 | 86-88 | 171-183 |
| 30 | 75-84 | 83-85 | 158-170 |
| 20 | 74 - | 82 - | 157 - |

FIG. 6B(4)

| Scale | Ball Velocity Off Bat (MPH) | Glove to Release (Timed) | Score | Scale | Ball Velocity Off Bat (MPH) | Range (Left) | Range (Right) | Score | Scale | Ball Velocity Off Bat (MPH) | Throwing Accuracy % | Score |
|---|---|---|---|---|---|---|---|---|---|---|---|---|
| 80 | 125+ | .299- | 205+ | 80 | 125+ | 1.03- | 1.03- | 205+ | 80 | 125+ | 95+ | 220+ |
| 70 | 115-125 | .30-.399 | 185-204 | 70 | 115-125 | 1.0325-1.0525 | 1.0325-1.0525 | 185-204 | 70 | 115-124 | 90 | 205-219 |
| 60 | 105-114 | .40-.499 | 165-184 | 60 | 105-114 | 1.055-1.075 | 1.055-1.075 | 165-184 | 60 | 105-114 | 85 | 190-204 |
| 50 | 95-105 | .50-.599 | 145-164 | 50 | 95-105 | 1.0775-1.0975 | 1.0775-1.0975 | 145-164 | 50 | 95-104 | 80 | 175-189 |
| 40 | 85-95 | .60-.699 | 125-144 | 40 | 85-95 | 1.10-1.1225 | 1.10-1.1225 | 125-144 | 40 | 85-94 | 75 | 160-174 |
| 30 | 75-85 | .70-.799 | 105-124 | 30 | 75-85 | 1.125-1.1475 | 1.125-1.1475 | 105-124 | 30 | 75-84 | 70 | 145-159 |
| 20 | 75 - | .80+ | 104 - | 20 | 75 - | 1.25+ | 1.25+ | 104 - | 20 | 75 - | 65 - | 144 - |

FIG. 6B(5)

| Scale | Barrel Accuracy % | Arm Strength (MPH) | Score | Scale | Barrel Accuracy % | Range (Left) | Range (Right) | Score | Scale | Barrel Accuracy % | Barrel Angle at Contact % | Score |
|---|---|---|---|---|---|---|---|---|---|---|---|---|
| 80 | 98+ | 90+ | 188+ | 80 | 98+ | 1.03- | 1.03- | 178+ | 80 | 98+ | 98+ | 196-200 |
| 70 | 95-97 | 87-89 | 182-187 | 70 | 95-97 | 1.0325-1.0525 | 1.0325-1.0525 | 165-177 | 70 | 95-97 | 95-97 | 190-195 |
| 60 | 92-94 | 83-86 | 175-181 | 60 | 92-94 | 1.055-1.075 | 1.055-1.075 | 152-164 | 60 | 92-94 | 92-94 | 184-189 |
| 50 | 89-91 | 79-82 | 168-174 | 50 | 89-91 | 1.0775-1.0975 | 1.0775-1.0975 | 139-151 | 50 | 89-91 | 89-91 | 178-183 |
| 40 | 86-88 | 75-78 | 161-167 | 40 | 86-88 | 1.10-1.1225 | 1.10-1.1225 | 126-138 | 40 | 86-88 | 86-88 | 172-177 |
| 30 | 83-85 | 74-77 | 157-160 | 30 | 83-85 | 1.125-1.1475 | 1.125-1.1475 | 113-125 | 30 | 83-85 | 83-85 | 166-171 |
| 20 | 82- | 70- | 156- | 20 | 82- | 1.25+ | 1.25+ | 112- | 20 | 82- | 82- | 165- |

FIG. 6B(6)

| Scale | Barrel Accuracy % | Glove to Release (Timed) | Score | Scale | Barrel Accuracy % | Throwing Accuracy % | Score |
|---|---|---|---|---|---|---|---|
| 80 | 98+ | .299- | 178+ | 80 | 98+ | 95+ | 193-195 |
| 70 | 95-97 | .30-.399 | 165-177 | 70 | 95-97 | 90 | 185-187 |
| 60 | 92-94 | .40-.499 | 152-164 | 60 | 92-94 | 85 | 177-184 |
| 50 | 89-91 | .50-.599 | 139-151 | 50 | 89-91 | 80 | 169-176 |
| 40 | 86-88 | .60-.699 | 126-138 | 40 | 86-88 | 75 | 161-168 |
| 30 | 83-85 | .70-.799 | 113-125 | 30 | 83-85 | 70 | 153-160 |
| 20 | 82- | .80+ | 112- | 20 | 82- | 65- | 152- |

Fielding

| Scale | Glove to Release (Timed) | Arm Strength (MPH) | Throwing Accuracy % | Range (Left) | Range (Right) | Score |
|---|---|---|---|---|---|---|
| 80 | .299- | 90+ | 95+ | 1.03- | 1.03- | 345+ |
| 70 | .30-.399 | 87-89 | 90 | 1.0325-1.0525 | 1.0325-1.0525 | 317-344 |
| 60 | .40-.499 | 83-86 | 85 | 1.055-1.075 | 1.055-1.075 | 288-316 |
| 50 | .50-.599 | 79-82 | 80 | 1.0775-1.0975 | 1.0775-1.0975 | 259-287 |
| 40 | .60-.699 | 75-78 | 75 | 1.10-1.1225 | 1.10-1.1225 | 230-258 |
| 30 | .70-.799 | 74-77 | 70 | 1.125-1.1475 | 1.125-1.1475 | 204-229 |
| 20 | .80+ | 70- | 65- | 1.25+ | 1.25+ | 203- |

| Scale | Arm Strength (MPH) | Throwing Accuracy % | Score |
|---|---|---|---|
| 80 | 90+ | 95+ | 185+ |
| 70 | 87-89 | 90 | 177-184 |
| 60 | 83-86 | 85 | 168-176 |
| 50 | 79-82 | 80 | 159-167 |
| 40 | 75-78 | 75 | 150-158 |
| 30 | 74-77 | 70 | 144-149 |
| 20 | 73- | 69- | 143- |

| Scale | Arm Strength (MPH) | Glove to Release (Timed) | Score |
|---|---|---|---|
| 80 | 90+ | .299- | 170+ |
| 70 | 87-89 | .30-.399 | 157-169 |
| 60 | 83-86 | .40-.499 | 143-156 |
| 50 | 79-82 | .50-.599 | 129-142 |
| 40 | 75-78 | .60-.699 | 115-128 |
| 30 | 74-77 | .70-.799 | 104-114 |
| 20 | 70- | .80+ | 103- |

FIG. 7A

| Scale | Glove to Release (Timed) | Range (Left) | Range (Right) | Score | Scale | Arm Strength (MPH) | Range (Left) | Range (Right) | Score |
|---|---|---|---|---|---|---|---|---|---|
| 80 | .299- | 1.03- | 1.03- | 175+ | 80 | 90+ | 1.03- | 1.03- | 170+ |
| 70 | .30-.399 | 1.0325-1.0525 | 1.0325-1.0525 | 160-174 | 70 | 87-89 | 1.0325-1.0525 | 1.0325-1.0525 | 157-169 |
| 60 | .40-.499 | 1.055-1.075 | 1.055-1.075 | 145-169 | 60 | 83-86 | 1.055-1.075 | 1.055-1.075 | 143-156 |
| 50 | .50-.599 | 1.0775-1.0975 | 1.0775-1.0975 | 130-144 | 50 | 79-82 | 1.0775-1.0975 | 1.0775-1.0975 | 129-142 |
| 40 | .60-.699 | 1.10-1.1225 | 1.10-1.1225 | 120-129 | 40 | 75-78 | 1.10-1.1225 | 1.10-1.1225 | 115-128 |
| 30 | .70-.799 | 1.125-1.1475 | 1.125-1.1475 | 100-119 | 30 | 74-77 | 1.125-1.1475 | 1.125-1.1475 | 104-114 |
| 20 | .80+ | 1.25+ | 1.25+ | 99 - | 20 | 70 - | 1.25+ | 1.25+ | 103 - |

| Scale | Glove to Release (Timed) | Range (Left) | Range (Right) | Score | Scale | Throwing Accuracy % | Range (Left) | Range (Right) | Score |
|---|---|---|---|---|---|---|---|---|---|
| 80 | .299- | 1.03- | 1.03- | 1.329 - | 80 | 95+ | 1.03- | 1.03- | 175+ |
| 70 | .30-.399 | 1.0325-1.0525 | 1.0325-1.0525 | 1.332-1.451 | 70 | 90 | 1.0325-1.0525 | 1.0325-1.0525 | 160-174 |
| 60 | .40-.499 | 1.055-1.075 | 1.055-1.075 | 1.452-1.574 | 60 | 85 | 1.055-1.075 | 1.055-1.075 | 145-169 |
| 50 | .50-.599 | 1.0775-1.0975 | 1.0775-1.0975 | 1.575-1.696 | 50 | 80 | 1.0775-1.0975 | 1.0775-1.0975 | 130-144 |
| 40 | .60-.699 | 1.10-1.1225 | 1.10-1.1225 | 1.697-1.821 | 40 | 75 | 1.10-1.1225 | 1.10-1.1225 | 120-129 |
| 30 | .70-.799 | 1.125-1.1475 | 1.125-1.1475 | 1.822-1.946 | 30 | 70 | 1.125-1.1475 | 1.125-1.1475 | 100-119 |
| 20 | .80+ | 1.25+ | 1.25+ | 1.947+ | 20 | 69 - | 1.25+ | 1.25+ | 99 - |

Catching

| Scale | Glove to Release (Timed) | Arm Strength (MPH) | Throwing Accuracy % | Score |
|---|---|---|---|---|
| 80 | .299- | 90+ | 95+ | 265+ |
| 70 | .30-.399 | 87-89 | 90 | 247-264 |
| 60 | .40-.499 | 83-86 | 85 | 228-246 |
| 50 | .50-.599 | 79-82 | 80 | 209-227 |
| 40 | .60-.699 | 75-78 | 75 | 190-208 |
| 30 | .70-.799 | 71-74 | 70 | 171-189 |
| 20 | .80+ | 70- | 65- | 170- |

| Scale | Glove to Release (Timed) | Throwing Accuracy % | Score | Scale | Glove to Release (Timed) | Range (Left) | Range (Right) | Score |
|---|---|---|---|---|---|---|---|---|
| 80 | .299- | 95+ | 175+ | 80 | .299- | 1.03- | 1.03- | 1.329- |
| 70 | .30-.399 | 90 | 160-174 | 70 | .30-.399 | 1.0325-1.0525 | 1.0325-1.0525 | 1.332-1.451 |
| 60 | .40-.499 | 85 | 145-169 | 60 | .40-.499 | 1.055-1.075 | 1.055-1.075 | 1.452-1.574 |
| 50 | .50-.599 | 80 | 130-144 | 50 | .50-.599 | 1.0775-1.0975 | 1.0775-1.0975 | 1.575-1.696 |
| 40 | .60-.699 | 75 | 120-129 | 40 | .60-.699 | 1.10-1.1225 | 1.10-1.1225 | 1.697-1.821 |
| 30 | .70-.799 | 70 | 100-119 | 30 | .70-.799 | 1.125-1.1475 | 1.125-1.1475 | 1.822-1.946 |
| 20 | .80+ | 65- | 99- | 20 | .80+ | 1.25+ | 1.25+ | 1.947+ |

| Scale | Arm Strength (MPH) | Throwing Accuracy % | Score | Scale | Arm Strength (MPH) | Range (Left) | Range (Right) | Score |
|---|---|---|---|---|---|---|---|---|
| 80 | 90+ | 95+ | 185+ | 80 | 90+ | 1.03- | 1.03- | 170+ |
| 70 | 87-89 | 90 | 177-184 | 70 | 87-89 | 1.0325-1.0525 | 1.0325-1.0525 | 157-169 |
| 60 | 83-86 | 85 | 168-176 | 60 | 83-86 | 1.055-1.075 | 1.055-1.075 | 143-156 |
| 50 | 79-82 | 80 | 159-175 | 50 | 79-82 | 1.0775-1.0975 | 1.0775-1.0975 | 129-142 |
| 40 | 75-78 | 75 | 150-158 | 40 | 75-78 | 1.10-1.1225 | 1.10-1.1225 | 115-128 |
| 30 | 71-74 | 70 | 141-149 | 30 | 71-74 | 1.125-1.1475 | 1.125-1.1475 | 104-114 |
| 20 | 70- | 65- | 140 | 20 | 70- | 1.25+ | 1.25+ | 103- |

| Scale | Arm Strength (MPH) | Glove to Release (Timed) | Score |
|---|---|---|---|
| 80 | 90+ | .299- | 170+ |
| 70 | 87-89 | .30-.399 | 157-169 |
| 60 | 83-86 | .40-.499 | 143-156 |
| 50 | 79-82 | .50-.599 | 129-142 |
| 40 | 75-78 | .60-.699 | 115-128 |
| 30 | 71-74 | .70-.799 | 104-114 |
| 20 | 70- | .80+ | 103- |

FIG. 8

Running/Agility

FIG. 9A(1)

| Scale | Home to First 90' (Right Side) | Home to First 90' (Left Side) | 40 Yard Time (Seconds) | 60 Yard Time (Seconds) | Acceleration 10 Yard Split (Seconds) | 20 Yard Short Shuttle (Seconds) | Score |
|---|---|---|---|---|---|---|---|
| 80 | 4- | 3.9- | 4.39- | 6.4- | 1.5- | 4.12- | 24.31- |
| 70 | 4.1 | 4 | 4.40-4.50 | 6.5-6.6 | 1.6 | 4.13-4.21 | 24.73-24.32 |
| 60 | 4.2 | 4.1 | 4.51-4.70 | 6.7-6.8 | 1.7 | 4.22-4.30 | 25.43-24.74 |
| 50 | 4.3 | 4.2 | 4.71-4.90 | 6.9-7.0 | 1.8 | 4.31-4.39 | 26.22-25.44 |
| 40 | 4.4 | 4.3 | 4.91-5.10 | 7.1-7.2 | 1.9 | 4.40-4.49 | 27.01-26.23 |
| 30 | 4.5 | 4.4 | 5.11-5.30 | 7.3-7.4 | 2.0 | 4.50-4.59 | 27.81-27.02 |
| 20 | 4.6+ | 4.5+ | 5.30+ | 7.5+ | 2.1+ | 5.0+ | 27.82+ |

FIG. 9A(2)

| Scale | Standing Long Jump (Feet) | Vertical Jump (Inches) | Score |
|---|---|---|---|
| 80 | 9.0+ | 36+ | 45+ |
| 70 | 8.6-8.9 | 33-35 | 41.6-44.9 |
| 60 | 8.2-8.5 | 30-32 | 38.2-41.5 |
| 50 | 7.8-8.1 | 27-29 | 34.8-38.1 |
| 40 | 7.4-7.7 | 24-26 | 31.4-34.7 |
| 30 | 7.1-7.3 | 21-23 | 28-31.3 |
| 20 | 7.0- | 20- | 27.99- |

FIG. 9A(3)

| Scale | 60 Yard Time (Seconds) | Arm Strength (MPH) | Score | Scale | 60 Yard Time (Seconds) | Bat Speed (MPH) | Score | Scale | 60 Yard Time (Seconds) | Barrel Angle at Contact % | Score |
|---|---|---|---|---|---|---|---|---|---|---|---|
| 80 | 6.4- | 90+ | 170+ | 800 | 6.4- | 95+ | 175+ | 800 | 6.4- | 98+ | 178+ |
| 70 | 6.5-6.6 | 87-89 | 157-169 | 700 | 6.5-6.6 | 90-94 | 160-174 | 700 | 6.5-6.6 | 95-97 | 165-177 |
| 60 | 6.7-6.8 | 83-86 | 143-156 | 600 | 6.7-6.8 | 85-89 | 145-159 | 600 | 6.7-6.8 | 92-94 | 152-164 |
| 50 | 6.9-7.0 | 79-82 | 129-142 | 500 | 6.9-7.0 | 80-84 | 130-144 | 500 | 6.9-7.0 | 89-91 | 139-151 |
| 40 | 7.1-7.2 | 75-78 | 115-128 | 400 | 7.1-7.2 | 75-79 | 115-129 | 400 | 7.1-7.2 | 86-88 | 126-138 |
| 30 | 7.3-7.4 | 74-77 | 104-114 | 300 | 7.3-7.4 | 70-74 | 100-114 | 300 | 7.3-7.4 | 83-85 | 113-125 |
| 20 | 7.5+ | 70- | 103- | 200 | 7.5+ | 70- | 99- | 200 | 7.5+ | 82- | 112- |

Running/Agility

| Scale | 60 Yard Time (Seconds) | Ball Velocity Off Bat (MPH) | Score | Scale | 60 Yard Time (Seconds) | Barrel Accuracy % | Score |
|---|---|---|---|---|---|---|---|
| 80 | 6.4- | 125+ | 205+ | 80 | 6.4- | 98+ | 178+ |
| 70 | 6.5-6.6 | 115-125 | 185-204 | 70 | 6.5-6.6 | 95-97 | 165-177 |
| 60 | 6.7-6.8 | 105-115 | 165-184 | 60 | 6.7-6.8 | 92-94 | 152-164 |
| 50 | 6.9-7.0 | 95-105 | 145-164 | 50 | 6.9-7.0 | 89-91 | 139-151 |
| 40 | 7.1-7.2 | 85-95 | 125-144 | 40 | 7.1-7.2 | 86-88 | 126-138 |
| 30 | 7.3-7.4 | 75-85 | 105-124 | 30 | 7.3-7.4 | 83-85 | 113-125 |
| 20 | 7.5+ | 75- | 104- | 20 | 7.5+ | 82- | 112- |

FIG. 9A(4)

| Scale | 60 Yard Time (Seconds) | Distance (Feet) | Score | Scale | 60 Yard Time (Seconds) | Glove to Release (Timed) | Score |
|---|---|---|---|---|---|---|---|
| 80 | 6.4- | 425+ | 505+ | 80 | 6.4- | .299- | 6.7- |
| 70 | 6.5-6.6 | 400-425 | 470-504 | 70 | 6.5-6.6 | .30-.399 | 6.71-6.99 |
| 60 | 6.7-6.8 | 375-400 | 435-469 | 60 | 6.7-6.8 | .40-.499 | 7-7.299 |
| 50 | 6.9-7.0 | 350-375 | 400-434 | 50 | 6.9-7.0 | .50-.599 | 7.3-7.599 |
| 40 | 7.1-7.2 | 325-350 | 365-399 | 40 | 7.1-7.2 | .60-.699 | 7.6-7.899 |
| 30 | 7.3-7.4 | 300-325 | 330-364 | 30 | 7.3-7.4 | .70-.799 | 7.9-8.199 |
| 20 | 7.5+ | 300- | 329- | 20 | 7.5+ | .80+ | 8.2+ |

| Scale | 60 Yard Time (Seconds) | Range (Left) | Range (Right) | Score | Scale | 60 Yard Time (Seconds) | Vertical Jump (Inches) | Score |
|---|---|---|---|---|---|---|---|---|
| 80 | 6.4- | 1.03- | 1.03- | 7.43- | 80 | 6.4- | 36+ | 116+ |
| 70 | 6.5-6.6 | 1.0325-1.0525 | 1.0325-1.0525 | 7.532-7.652 | 70 | 6.5-6.6 | 33-35 | 103-115 |
| 60 | 6.7-6.8 | 1.055-1.075 | 1.055-1.075 | 7.653-7.875 | 60 | 6.7-6.8 | 30-32 | 90-102 |
| 50 | 6.9-7.0 | 1.0775-1.0975 | 1.0775-1.0975 | 7.876-8.097 | 50 | 6.9-7.0 | 27-29 | 77-89 |
| 40 | 7.1-7.2 | 1.10-1.1225 | 1.10-1.1225 | 8.098-8.322 | 40 | 7.1-7.2 | 24-26 | 64-76 |
| 30 | 7.3-7.4 | 1.125-1.1475 | 1.125-1.1475 | 8.323-8.547 | 30 | 7.3-7.4 | 21-23 | 51-63 |
| 20 | 7.5+ | 1.25+ | 1.25+ | 8.548+ | 20 | 7.5+ | 20- | 50- |

FIG. 9B(2)

| Scale | 60 Yard Time (Seconds) | Throwing Accuracy Percentage | Score | Scale | 60 Yard Time (Seconds) | Standing Long Jump (Feet) | Score |
|---|---|---|---|---|---|---|---|
| 80 | 6.4- | 95+ | 175+ | 80 | 6.4- | 9.0+ | 89+ |
| 70 | 6.5-6.6 | 90 | 160-174 | 70 | 6.5-6.6 | 8.6-8.9 | 78.6-88.9 |
| 60 | 6.7-6.8 | 85 | 145-159 | 60 | 6.7-6.8 | 8.2-8.5 | 68.2-78.5 |
| 50 | 6.9-7.0 | 80 | 130-144 | 50 | 6.9-7.0 | 7.8-8.1 | 57.8-68.1 |
| 40 | 7.1-7.2 | 75 | 115-129 | 40 | 7.1-7.2 | 7.4-7.7 | 47.4-57.7 |
| 30 | 7.3-7.4 | 70 | 100-114 | 30 | 7.3-7.4 | 7.1-7.3 | 37.1-47.3 |
| 20 | 7.5+ | 65- | 99- | 20 | 7.5+ | 7.0- | 37- |

| Scale | 60 Yard Time (Seconds) | Acceleration 10 Yard Split (Seconds) | Score | 60 Yard Time (Seconds) | Home to First 90' (Right Side) | Home to First 90' (Left Side) | Score Right | Score Left |
|---|---|---|---|---|---|---|---|---|
| 80 | 6.4- | 1.5- | 7.9- | 6.4- | 4- | 3.9- | 10.4- | 10.3- |
| 70 | 6.5-6.6 | 1.6 | 7.91-8.2 | 6.5-6.6 | 4.1 | 4 | 10.41-10.7 | 10.31-10.6 |
| 60 | 6.7-6.8 | 1.7 | 8.21-8.50 | 6.7-6.8 | 4.2 | 4.1 | 10.71-11 | 10.61-10.9 |
| 50 | 6.9-7.0 | 1.8 | 8.51-8.80 | 6.9-7.0 | 4.3 | 4.2 | 11.1-11.3 | 10.91-11.2 |
| 40 | 7.1-7.2 | 1.9 | 8.81-9.10 | 7.1-7.2 | 4.4 | 4.3 | 11.31-11.6 | 11.21-11.5 |
| 30 | 7.3-7.4 | 2.0 | 9.11-9.40 | 7.3-7.4 | 4.5 | 4.4 | 11.81-11.9 | 11.51-11.8 |
| 20 | 7.5+ | 2.1+ | 9.41+ | 7.5+ | 4.6+ | 4.5+ | 11.91+ | 11.81+ |

| Scale | Home to First 90' (Right Side) | Home to First 90' (Left Side) | Arm Strength (MPH) | Score Right Side | Score Left Side | Scale | Home to First 90' (Right Side) | Home to First 90' (Left Side) | Bat Speed (MPH) | Score | Score |
|---|---|---|---|---|---|---|---|---|---|---|---|
| 80 | 4- | 3.9- | 90+ | 170+ | 170+ | 80 | 4- | 3.9- | 95+ | 175+ | 175+ |
| 70 | 4.1 | 4 | 87-89 | 157-169 | 157-169 | 70 | 4.1 | 4 | 90-94 | 160-174 | 160-174 |
| 60 | 4.2 | 4.1 | 83-86 | 143-156 | 143-156 | 60 | 4.2 | 4.1 | 85-89 | 145-159 | 145-159 |
| 50 | 4.3 | 4.2 | 79-82 | 129-142 | 129-142 | 50 | 4.3 | 4.2 | 80-84 | 130-144 | 130-144 |
| 40 | 4.4 | 4.3 | 75-78 | 115-128 | 115-128 | 40 | 4.4 | 4.3 | 75-79 | 115-129 | 115-129 |
| 30 | 4.5 | 4.4 | 74-77 | 104-114 | 104-114 | 30 | 4.5 | 4.4 | 70-74 | 100-114 | 100-114 |
| 20 | 4.6+ | 4.5+ | 70- | 103- | 103- | 20 | 4.6+ | 4.5+ | 70- | 99- | 99- |

FIG. 9C(2)

| Scale | Home to First 90' (Right Side) | Home to First 90' (Left Side) | Distance (Feet) | Score Right Side | Score Left Side | Scale | Home to First 90' (Right Side) | Home to First 90' (Left Side) | Ball Velocity Off Bat (MPH) | Score | Score |
|---|---|---|---|---|---|---|---|---|---|---|---|
| 80 | 4- | 3.9- | 425+ | 505+ | 505+ | 80 | 4- | 3.9- | 125+ | 205+ | 205+ |
| 70 | 4.1 | 4 | 400-425 | 470-504 | 470-504 | 70 | 4.1 | 4 | 115-125 | 185-204 | 185-204 |
| 60 | 4.2 | 4.1 | 375-400 | 435-469 | 435-469 | 60 | 4.2 | 4.1 | 105-115 | 165-184 | 165-184 |
| 50 | 4.3 | 4.2 | 350-375 | 400-434 | 400-434 | 50 | 4.3 | 4.2 | 95-105 | 145-164 | 145-164 |
| 40 | 4.4 | 4.3 | 325-350 | 365-399 | 365-399 | 40 | 4.4 | 4.3 | 85-95 | 125-144 | 125-144 |
| 30 | 4.5 | 4.4 | 300-325 | 330-364 | 330-364 | 30 | 4.5 | 4.4 | 75-85 | 105-124 | 105-124 |
| 20 | 4.6+ | 4.5+ | 300- | 329- | 329- | 20 | 4.6+ | 4.5+ | 75- | 104- | 104- |

| Scale | Home to First 90' (Right Side) | Home to First 90' (Left Side) | Throwing Accuracy % | Score Right Side | Score Left Side |
|---|---|---|---|---|---|
| 80 | 4- | 3.9- | 95+ | 175+ | 175+ |
| 70 | 4.1 | 4 | 90 | 160-174 | 160-174 |
| 60 | 4.2 | 4.1 | 85 | 145-159 | 145-159 |
| 50 | 4.3 | 4.2 | 80 | 130-144 | 130-144 |
| 40 | 4.4 | 4.3 | 75 | 115-129 | 115-129 |
| 30 | 4.5 | 4.4 | 70 | 100-114 | 100-114 |
| 20 | 4.6+ | 4.5+ | 65- | 99- | 99- |

| Scale | Home to First 90' (Right Side) | Home to First 90' (Left Side) | Barrel Accuracy % | Score Right Side | Score Left Side |
|---|---|---|---|---|---|
| 80 | 4- | 3.9- | 98+ | 178+ | 178+ |
| 70 | 4.1 | 4 | 95-97 | 165-177 | 165-177 |
| 60 | 4.2 | 4.1 | 92-94 | 152-164 | 152-164 |
| 50 | 4.3 | 4.2 | 89-91 | 139-151 | 139-151 |
| 40 | 4.4 | 4.3 | 86-88 | 126-138 | 126-138 |
| 30 | 4.5 | 4.4 | 83-85 | 113-125 | 113-125 |
| 20 | 4.6+ | 4.5+ | 82- | 112- | 112- |

FIG. 9C(3)

| Scale | Home to First 90' (Right Side) | Home to First 90' (Left Side) | Glove to Release (Timed) | Score Right Side | Score Left Side |
|---|---|---|---|---|---|
| 80 | 4- | 3.9- | .299- | 4.299- | 4.199- |
| 70 | 4.1 | 4 | .30-.399 | 4.298-4.4 | 4.198-4.3 |
| 60 | 4.2 | 4.1 | .40-.499 | 4.41-4.6 | 4.31-4.5 |
| 50 | 4.3 | 4.2 | .50-.599 | 4.61-4.8 | 4.51-4.7 |
| 40 | 4.4 | 4.3 | .60-.699 | 4.81-5.0 | 4.71-4.9 |
| 30 | 4.5 | 4.4 | .70-.799 | 5.01-5.2 | 4.91-5.1 |
| 20 | 4.6+ | 4.5+ | .80+ | 5.21+ | 5.11+ |

| Scale | Home to First 90' (Right Side) | Home to First 90' (Left Side) | Range (Left) | Range (Right) | Score Right Side | Score Left Side |
|---|---|---|---|---|---|---|
| 80 | 4- | 3.9- | 1.03+ | 1.03+ | 5.03- | 5.03- |
| 70 | 4.1 | 4 | 1.0325-1.0525 | 1.0325-1.0525 | 5.031-5.152 | 5.031-5.052 |
| 60 | 4.2 | 4.1 | 1.055-1.075 | 1.055-1.075 | 5.255-5.275 | 5.155-5.175 |
| 50 | 4.3 | 4.2 | 1.0775-1.0975 | 1.0775-1.0975 | 5.377-5.397 | 5.277-5.297 |
| 40 | 4.4 | 4.3 | 1.10-1.1225 | 1.10-1.1225 | 5.5-5.522 | 5.4-5.422 |
| 30 | 4.5 | 4.4 | 1.125-1.1475 | 1.125-1.1475 | 5.625-5.647 | 5.525-5.547 |
| 20 | 4.6+ | 4.5+ | 1.25+ | 1.25+ | 5.648+ | 5.548+ |

| Scale | Home to First 90' (Right Side) | Home to First 90' (Left Side) | Vertical Jump (Inches) | Score Right Side | Score Left Side | Scale | Home to First 90' (Right Side) | Home to First 90' (Left Side) | Standing Long Jump (Feet) | Score | Scale | Home to First 90' (Right Side) | Home to First 90' (Left Side) | Barrel Angle at Contact % | Score | Score |
|---|---|---|---|---|---|---|---|---|---|---|---|---|---|---|---|---|
| 80 | 4- | 3.9- | 36+ | 116+ | 116+ | 80 | 4- | 3.9- | 9.0+ | 89+ | 80 | 4- | 3.9- | 98+ | 178+ | 178+ |
| 70 | 4.1 | 4 | 33-35 | 103-115 | 103-115 | 70 | 4.1 | 4 | 8.6-8.9 | 78.6-88.9 | 70 | 4.1 | 4 | 95-97 | 165-177 | 165-177 |
| 60 | 4.2 | 4.1 | 30-32 | 90-102 | 90-102 | 60 | 4.2 | 4.1 | 8.2-8.5 | 68.2-78.5 | 60 | 4.2 | 4.1 | 92-94 | 152-164 | 152-164 |
| 50 | 4.3 | 4.2 | 27-29 | 77-89 | 77-89 | 50 | 4.3 | 4.2 | 7.8-8.1 | 57.8-68.1 | 50 | 4.3 | 4.2 | 89-91 | 139-151 | 139-151 |
| 40 | 4.4 | 4.3 | 24-26 | 64-76 | 64-76 | 40 | 4.4 | 4.3 | 7.4-7.7 | 47.4-57.7 | 40 | 4.4 | 4.3 | 86-88 | 126-138 | 126-138 |
| 30 | 4.5 | 4.4 | 21-23 | 51-63 | 51-63 | 30 | 4.5 | 4.4 | 7.1-7.3 | 37.1-47.3 | 30 | 4.5 | 4.4 | 83-85 | 113-125 | 113-125 |
| 20 | 4.6+ | 4.5+ | 20- | 50- | 50- | 20 | 4.6+ | 4.5+ | 7.0- | 37- | 20 | 4.6+ | 4.5+ | 82- | 112- | 112- |

FIG. 9D(2)

| Scale | Home to First 90' (Right Side) | Home to First 90' (Left Side) | Acceleration 10 Yard Split (Seconds) | Score Right Side | Score Left Side | Scale | Vertical Jump (Inches) | Standing Long Jump (Feet) | Score |
|---|---|---|---|---|---|---|---|---|---|
| 80 | 4- | 3.9- | 1.5- | 5.5- | 5.4- | 80 | 36+ | 9.0+ | 45+ |
| 70 | 4.1 | 4 | 1.6 | 5.6-5.7 | 5.5-5.6 | 70 | 33-35 | 8.6-8.9 | 41.6-44.9 |
| 60 | 4.2 | 4.1 | 1.7 | 5.8-5.9 | 5.7-5.8 | 60 | 30-32 | 8.2-8.5 | 38.2-41.5 |
| 50 | 4.3 | 4.2 | 1.8 | 6.0-6.1 | 5.9-6.0 | 50 | 27-29 | 7.8-8.1 | 34.8-38.1 |
| 40 | 4.4 | 4.3 | 1.9 | 6.2-6.3 | 6.1-6.2 | 40 | 24-26 | 7.4-7.7 | 31.4-34.7 |
| 30 | 4.5 | 4.4 | 2.0 | 6.4-6.5 | 6.3-6.4 | 30 | 21-23 | 7.1-7.3 | 28-31.3 |
| 20 | 4.6+ | 4.5+ | 2.1+ | 6.6+ | 6.5+ | 20 | 20- | 7.0- | 27.99- |

FIG. 9D(3)

| Scale | Acceleration 10 Yard Split (Seconds) | Barrel Angle at Contact % | Score |
|---|---|---|---|
| 80 | 1.5- | 98+ | 178+ |
| 70 | 1.6 | 95-97 | 165-177 |
| 60 | 1.7 | 92-94 | 152-164 |
| 50 | 1.8 | 89-91 | 139-151 |
| 40 | 1.9 | 86-88 | 126-138 |
| 30 | 2.0 | 83-85 | 113-125 |
| 20 | 2.1+ | 82- | 112- |

FIG. 9D(4)

| Scale | Acceleration 10 Yard Split (Seconds) | Throwing Accuracy % | Score | Scale | Standing Long Jump (Feet) | Range (Left) | Range (Right) | Score | Score |
|---|---|---|---|---|---|---|---|---|---|
| 80 | 1.5- | 95+ | 175+ | 80 | 9.0+ | 1.03- | 1.03- | 89+ | 89+ |
| 70 | 1.6 | 90 | 160-174 | 70 | 8.6-8.9 | 1.0325-1.0525 | 1.0325-1.0525 | 78.6-88.9 | 78.6-88.9 |
| 60 | 1.7 | 85 | 145-159 | 60 | 8.2-8.5 | 1.055-1.075 | 1.055-1.075 | 68.2-78.5 | 68.2-78.5 |
| 50 | 1.8 | 80 | 130-144 | 50 | 7.8-8.1 | 1.0775-1.0975 | 1.0775-1.0975 | 57.8-68.1 | 57.8-68.1 |
| 40 | 1.9 | 75 | 115-129 | 40 | 7.4-7.7 | 1.10-1.1225 | 1.10-1.1225 | 47.4-57.7 | 47.4-57.7 |
| 30 | 2.0 | 70 | 104-114 | 30 | 7.1-7.3 | 1.125-1.1475 | 1.125-1.1475 | 37.1-47.3 | 37.1-47.3 |
| 20 | 2.1+ | 65 - | 99 - | 20 | 7.0- | 1.25+ | 1.25+ | 37 - | 37 - |

FIG. 9D(5)

| Scale | Acceleration 10 Yard Split (Seconds) | Arm Strength (MPH) | Score | Scale | Acceleration 10 Yard Split (Seconds) | Bat Speed (MPH) | Score |
|---|---|---|---|---|---|---|---|
| 80 | 1.5- | 90+ | 170+ | 80 | 1.5- | 95+ | 175+ |
| 70 | 1.6 | 87-89 | 157-169 | 70 | 1.6 | 90-94 | 160-174 |
| 60 | 1.7 | 83-86 | 143-156 | 60 | 1.7 | 85-89 | 145-159 |
| 50 | 1.8 | 79-82 | 129-142 | 50 | 1.8 | 80-84 | 130-144 |
| 40 | 1.9 | 75-78 | 115-128 | 40 | 1.9 | 75-79 | 115-129 |
| 30 | 2.0 | 74-77 | 104-114 | 30 | 2.0 | 70-74 | 100-114 |
| 20 | 2.1+ | 70 - | 103 - | 20 | 2.1+ | 70 - | 99 - |

FIG. 9D(6)

| Scale | Acceleration 10 Yard Split (Seconds) | Barrel Accuracy % | Score | Scale | Acceleration 10 Yard Split (Seconds) | Glove to Release (Timed) | Score |
|---|---|---|---|---|---|---|---|
| 80 | 1.5- | 98+ | 178+ | 80 | 1.5- | .299- | 1799- |
| 70 | 1.6 | 95-97 | 165-177 | 70 | 1.6 | .30-.399 | 1.8-1.999 |
| 60 | 1.7 | 92-94 | 152-164 | 60 | 1.7 | .40-.499 | 2.0-2.199 |
| 50 | 1.8 | 89-91 | 139-151 | 50 | 1.8 | .50-.599 | 2.2-2.399 |
| 40 | 1.9 | 86-88 | 126-138 | 40 | 1.9 | .60-.699 | 2.4-2.599 |
| 30 | 2.0 | 83-85 | 113-125 | 30 | 2.0 | .70-.799 | 2.6-2.799 |
| 20 | 2.1+ | 82- | 112- | 20 | 2.1+ | .80+ | 2.8+ |

FIG. 9D(7)

| Scale | Acceleration 10 Yard Split (Seconds) | Ball Velocity Off Bat (MPH) | Score | Scale | Acceleration 10 Yard Split (Seconds) | Distance (Feet) | Score |
|---|---|---|---|---|---|---|---|
| 80 | 1.5- | 125+ | 205+ | 80 | 1.5- | 425+ | 505+ |
| 70 | 1.6 | 115-125 | 185-204 | 70 | 1.6 | 400-425 | 470-504 |
| 60 | 1.7 | 105-115 | 165-184 | 60 | 1.7 | 375-400 | 435-469 |
| 50 | 1.8 | 95-105 | 145-164 | 50 | 1.8 | 350-375 | 400-434 |
| 40 | 1.9 | 85-95 | 125-144 | 40 | 1.9 | 325-350 | 365-399 |
| 30 | 2.0 | 75-85 | 105-124 | 30 | 2.0 | 300-325 | 330-364 |
| 20 | 2.1+ | 75- | 104- | 20 | 2.1+ | 300- | 329- |

| Scale | Acceleration 10 Yard Split (Seconds) | Range (Left) | Range (Right) | Score | Scale | Vertical Jump (Inches) | Range (Left) | Range (Right) | Score | Score |
|---|---|---|---|---|---|---|---|---|---|---|
| 80 | 1.5- | 1.03- | 1.03- | 2.53- | 80 | 36+ | 1.03- | 1.03- | 116+ | 116+ |
| 70 | 1.6 | 1.0325-1.0525 | 1.0325-1.0525 | 2.54-2.65 | 70 | 33-35 | 1.0325-1.0525 | 1.0325-1.0525 | 103-115 | 103-115 |
| 60 | 1.7 | 1.055-1.075 | 1.055-1.075 | 2.66-2.77 | 60 | 30-32 | 1.055-1.075 | 1.055-1.075 | 90-102 | 90-102 |
| 50 | 1.8 | 1.0775-1.0975 | 1.0775-1.0975 | 2.78-2.89 | 50 | 27-29 | 1.0775-1.0975 | 1.0775-1.0975 | 77-89 | 77-89 |
| 40 | 1.9 | 1.10-1.1225 | 1.10-1.1225 | 2.90-3.02 | 40 | 24-26 | 1.10-1.1225 | 1.10-1.1225 | 64-76 | 64-76 |
| 30 | 2.0 | 1.125-1.1475 | 1.125-1.1475 | 3.03-3.15 | 30 | 21-23 | 1.125-1.1475 | 1.125-1.1475 | 51-63 | 51-63 |
| 20 | 2.1+ | 1.25+ | 1.25+ | 3.16+ | 20 | 20- | 1.25+ | 1.25+ | 50- | 50- |

FIG. 9D(8)

Football Parameters (Quarterback)

| Scale | 40 Yard Time | 60 Yard Time | 10 Yard Split | 20 Yard Short Shuttle | 60 Yard Long Shuttle | 3 Step Drop Time | 5 Step Drop Time | 7 Step Drop Time | Release Time | Reaction Time | Compression Force Drive | 3 Cone Drill | Score |
|---|---|---|---|---|---|---|---|---|---|---|---|---|---|
| 9.00-10 | 4.80 - | 6.4 - | 1.4 - | 4.35 - | 10.5 - | 2.0 - | 2.5 - | 3.0 - | .299 | 0.0-.15 | 180 psi+ | 6.9 - | 188+ |
| 8.00-8.99 | 4.81-4.90 | 6.5-6.6 | 1.41-1.55 | 4.36-4.45 | 10.6-11.0 | 2.1-2.2 | 2.6-2.7 | 3.1-3.2 | .30-.399 | .16-.20 | 160-179 | 6.91-7.29 | 178-187 |
| 7.00-8.99 | 4.91-5.0 | 6.7-6.8 | 1.56-1.70 | 4.46-4.55 | 11.1-11.5 | 2.3-2.4 | 2.8-2.9 | 3.3-3.4 | .40-.499 | .21-.25 | 140-159 | 7.30-7.69 | 170-177 |
| 6.00-6.99 | 5.01-5.1 | 6.9-7.0 | 1.71-1.85 | 4.56-4.65 | 11.6-12.0 | 2.5-2.6 | 3.0-3.1 | 3.5-3.6 | .50-.599 | .26-.30 | 120-139 | 7.70-8.09 | 163-169 |
| 5.00-5.99 | 5.11+ | 7.1-7.2 | 1.86+ | 4.66+ | 12.1+ | 2.7+ | 3.2+ | 3.7+ | .60+ | .31+ | 119 - | 8.1+ | 155-162 |

FIG. 10A(1)

| Scale | Bench Press | Broad Jump | Vertical Jump | Arm Speed (MPH) | Throwing Accuracy % | Compression Force Rate | Score |
|---|---|---|---|---|---|---|---|
| 9.00-10 | 15+ | 9.5+ | 33+ | 75+ | 90+ | 180 psi+ | 402+ |
| 8.00-8.99 | 12-14 | 9-9.49 | 30-32 | 71-74 | 85-89 | 160-179 | 367-401 |
| 7.00-7.99 | 10-11 | 8.5-8.99 | 28-29 | 67-70 | 80-84 | 140-159 | 334-366 |
| 6.00-6.99 | 8-9 | 8-8.49 | 26-27 | 59-62 | 75-79 | 120-139 | 296-333 |
| 5.00-5.99 | 7 - | 7.99 - | 25 - | 58 - | 74 - | 119 - | 295 - |

FIG. 10A(2)

Football Parameters (Running Back)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 4.55 - | 6.4 - | 1.4 - | 4.25 - | 10.5 - | 7 - | 6.9 - | 30.05 - | 9.00-10 | 18+ | 35+ | 9.5+ | 180 psi+ | 242+ |
| 8.00-8.99 | 4.56-4.65 | 6.5-6.6 | 1.41-1.55 | 4.26-4.35 | 10.6-11.0 | 7.75-7.01 | 6.91-7.29 | 31.20-30.06 | 8.00-8.99 | 15-17 | 32-34 | 9-9.49 | 160-179 | 216-241 |
| 7.00-8.99 | 4.66-4.75 | 6.7-6.8 | 1.56-1.70 | 4.36-4.45 | 11.1-11.5 | 8.85-7.76 | 7.30-7.69 | 33.10-31.21 | 7.00-8.99 | 13-14 | 30-31 | 8.5-8.99 | 140-159 | 192-215 |
| 6.00-6.99 | 4.76-4.85 | 6.9-7.0 | 1.71-1.85 | 4.46-4.55 | 11.6-12.0 | 9.25-8.86 | 7.70-8.09 | 35.35-33.11 | 6.00-6.99 | 12-Nov | 28-29 | 8-8.49 | 120-139 | 167-191 |
| 5.00-5.99 | 4.86+ | 7.1-7.2 | 1.86+ | 4.56+ | 12.1+ | 9.26+ | 8.1+ | 35.36+ | 5.00-5.99 | 10 - | 27 - | 7.99 - | 119 - | 166 - |

*FIG. 10A(3)*

Football Parameters (Full Back)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 4.65 - | 6.4 - | 1.4 - | 4.30 - | 10.5 - | 7 - | 6.9 - | 41.15 - | 9.00-10 | 21+ | 31+ | 10+ | 180 psi+ | 242+ |
| 8.00-8.99 | 4.66-4.75 | 6.5-6.6 | 1.41-1.55 | 4.31-4.40 | 10.6-11.0 | 7.75-7.01 | 6.91-7.29 | 42.60-41.16 | 8.00-8.99 | 18-20 | 28-30 | 9.5-9.99 | 160-179 | 216-241 |
| 7.00-8.99 | 4.76-4.85 | 6.7-6.8 | 1.56-1.70 | 4.41-4.50 | 11.1-11.5 | 8.85-7.76 | 7.30-7.69 | 44.80-42.61 | 7.00-8.99 | 16-17 | 26-27 | 9-9.49 | 140-159 | 192-215 |
| 6.00-6.99 | 4.86-4.95 | 6.9-7.0 | 1.71-1.85 | 4.51-4.60 | 11.6-12.0 | 9.25-8.86 | 7.70-8.09 | 47.35-44.81 | 6.00-6.99 | 14-15 | 24-25 | 8.5-8.99 | 120-139 | 167-191 |
| 5.00-5.99 | 4.96+ | 7.1-7.2 | 1.86+ | 4.61+ | 12.1+ | 9.26+ | 8.1+ | 47.36+ | 5.00-5.99 | 13 - | 23 - | 8.49 - | 119 - | 166 - |

*FIG. 10A(4)*

Football Parameters (Wide Receiver)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 4.55 - | 6.4 - | 1.4 - | 4.2 - | 10.5 - | 7 - | 6.9 - | 40.95 - | 9.00-10 | 13+ | 35+ | 10+ | 180 psi+ | 238+ |
| 8.00-8.99 | 4.56-4.65 | 6.5-6.6 | 1.41-1.55 | 4.21-4.30 | 10.6-11.0 | 7.75-7.01 | 6.91-7.29 | 42.40-40.96 | 8.00-8.99 | 10-12 | 32-34 | 9.5-9.99 | 160-179 | 212-237 |
| 7.00-8.99 | 4.66-4.75 | 6.7-6.8 | 1.56-1.70 | 4.31-4.40 | 11.1-11.5 | 8.85-7.76 | 7.30-7.69 | 44.6-42.41 | 7.00-8.99 | 8-9 | 30-31 | 9-9.49 | 140-159 | 187-211 |
| 6.00-6.99 | 4.76-4.85 | 6.9-7.0 | 1.71-1.85 | 4.41-4.50 | 11.6-12.0 | 9.25-8.86 | 7.70-8.09 | 47.51-44.61 | 6.00-6.99 | 6-7 | 28-29 | 8.5-8.99 | 120-139 | 163-186 |
| 5.00-5.99 | 4.86+ | 7.1-7.2 | 1.86+ | 4.51+ | 12.1+ | 9.26+ | 8.1+ | 47.16+ | 5.00-5.99 | 5 - | 27 - | 8.49 - | 119 - | 162 - |

*FIG. 10A(5)*

Football Parameters (Tight End)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 4.75 | 6.4 - | 1.4 - | 4.40 - | 10.5 - | 7 - | 6.9 - | 41.35 - | 9.00-10 | 21+ | 31+ | 10+ | 180 psi+ | 242+ |
| 8.00-8.99 | 4.76-4.85 | 6.5-6.6 | 1.41-1.55 | 4.41-4.50 | 10.6-11.0 | 7.75-7.01 | 6.91-7.29 | 41.80-41.36 | 8.00-8.99 | 18-20 | 28-30 | 9.5-9.99 | 160-179 | 216-241 |
| 7.00-8.99 | 4.86-4.95 | 6.7-6.8 | 1.56-1.70 | 4.51-4.60 | 11.1-11.5 | 8.85-7.76 | 7.30-7.69 | 45-41.81 | 7.00-8.99 | 16-17 | 26-27 | 9-9.49 | 140-159 | 192-215 |
| 6.00-6.99 | 4.96-5.05 | 6.9-7.0 | 1.71-1.85 | 4.61-4.70 | 11.6-12.0 | 9.25-8.86 | 7.70-8.09 | 47.55-45.01 | 6.00-6.99 | 14-15 | 24-25 | 8.5-8.99 | 120-139 | 167-191 |
| 5.00-5.99 | 5.06+ | 7.1-7.2 | 1.86+ | 4.71+ | 12.1+ | 9.26+ | 8.1+ | 47.56+ | 5.00-5.99 | 13 - | 23 - | 8.49 - | 119 - | 166 - |

*FIG. 10A(6)*

Football Parameters (Offensive Linemen)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 5.24 - | 6.4 - | 1.4 - | 4.65 - | 10.5 - | 7 - | 6.9 - | 42.09 - | 9.00-10 | 27+ | 29+ | 8.5+ | 180 psi+ | 244+ |
| 8.00-8.99 | 5.25-5.35 | 6.5-6.6 | 1.41-1.55 | 4.66-4.75 | 10.6-11.0 | 7.75-7.01 | 6.91-7.29 | 42.55-42.10 | 8.00-8.99 | 24-26 | 28-26 | 8-8.49 | 160-179 | 218-243 |
| 7.00-8.99 | 5.36-5.45 | 6.7-6.8 | 1.56-1.70 | 4.76-4.85 | 11.1-11.5 | 8.85-7.76 | 7.30-7.69 | 45.75-42.56 | 7.00-8.99 | 22-23 | 24-25 | 7.5-7.99 | 140-159 | 194-217 |
| 6.00-6.99 | 5.46-5.55 | 6.9-7.0 | 1.71-1.85 | 4.86-4.95 | 11.6-12.0 | 9.25-8.86 | 7.70-8.09 | 48.30-45.76 | 6.00-6.99 | 20-21 | 22-23 | 7-7.49 | 120-139 | 169-193 |
| 5.00-5.99 | 5.56+ | 7.1-7.2 | 1.86+ | 4.96+ | 12.1+ | 9.26+ | 8.1+ | 48.31 - | 5.00-5.99 | 19 - | 21 - | 6.99 - | 119 - | 168 - |

FIG. 10A(7)

Football Parameters (Linebacker)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 4.74 - | 6.4 - | 1.4 - | 4.40 - | 10.5 - | 7 - | 6.9 - | 41.34 - | 9.00-10 | 23+ | 33+ | 9.5+ | 180 psi+ | 245+ |
| 8.00-8.99 | 4.75-4.84 | 6.5-6.6 | 1.41-1.55 | 4.41-4.50 | 10.6-11.0 | 7.75-7.01 | 6.91-7.29 | 42.79-41.34 | 8.00-8.99 | 20-22 | 30-32 | 9-9.49 | 160-179 | 219-244 |
| 7.00-8.99 | 4.85-4.94 | 6.7-6.8 | 1.56-1.70 | 4.51-4.60 | 11.1-11.5 | 8.85-7.76 | 7.30-7.69 | 44.99-42.80 | 7.00-8.99 | 18-19 | 28-29 | 8.5-8.99 | 140-159 | 194-218 |
| 6.00-6.99 | 4.95-5.04 | 6.9-7.0 | 1.71-1.85 | 4.61-4.70 | 11.6-12.0 | 9.25-8.86 | 7.70-8.09 | 47.54-45.0 | 6.00-6.99 | 16-17 | 26-27 | 8-8.49 | 120-139 | 170-193 |
| 5.00-5.99 | 5.05+ | 7.1-7.2 | 1.86+ | 4.71+ | 12.1+ | 9.26+ | 8.1+ | 47.55+ | 5.00-5.99 | 15 - | 25 - | 7.99 - | 119 - | 169 - |

FIG. 10B(1)

Football Parameters (Defensive Back)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 4.45 - | 6.4 - | 1.4 - | 4.20 - | 10.5 - | 7 - | 6.9 - | 40.85 - | 9.00-10 | 13+ | 35+ | 10+ | 180 psi+ | 238+ |
| 8.00-8.99 | 4.46-4.55 | 6.5-6.6 | 1.41-1.55 | 4.21-4.30 | 10.6-11.0 | 7.75-7.01 | 6.91-7.29 | 42.3-40.86 | 8.00-8.99 | 10-12 | 32-34 | 9.5-9.99 | 160-179 | 212-237 |
| 7.00-8.99 | 4.56-4.65 | 6.7-6.8 | 1.56-1.70 | 4.31-4.40 | 11.1-11.5 | 8.85-7.76 | 7.30-7.69 | 44.5-42.4 | 7.00-8.99 | 8-9 | 30-31 | 9-9.49 | 140-159 | 187-211 |
| 6.00-6.99 | 4.66-4.75 | 6.9-7.0 | 1.71-1.85 | 4.41-4.50 | 11.6-12.0 | 9.25-8.86 | 7.70-8.09 | 47.86-44.6 | 6.00-6.99 | 6-7 | 28-29 | 8.5-8.99 | 120-139 | 163-186 |
| 5.00-5.99 | 4.76+ | 7.1-7.2 | 1.86+ | 4.51+ | 12.1+ | 9.26+ | 8.1+ | 47.87+ | 5.00-5.99 | 5 - | 27 - | 8.49 - | 119 - | 162 - |

FIG. 10B(2)

Football Parameters (Safety)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 4.55 - | 6.4 - | 1.4 - | 4.25 - | 10.5 - | 7 - | 6.9 - | 41 - | 9.00-10 | 15+ | 35+ | 10+ | 180 psi+ | 240+ |
| 8.00-8.99 | 4.56-4.65 | 6.5-6.6 | 1.41-1.55 | 4.26-4.35 | 10.6-11.0 | 7.75-7.01 | 6.91-7.29 | 42.45-40.99 | 8.00-8.99 | 12-14 | 32-34 | 9.5-9.99 | 160-179 | 214-239 |
| 7.00-8.99 | 4.66-4.75 | 6.7-6.8 | 1.56-1.70 | 4.36-4.45 | 11.1-11.5 | 8.85-7.76 | 7.30-7.69 | 44.65-42.46 | 7.00-8.99 | 10-11 | 30-31 | 9-9.49 | 140-159 | 190-213 |
| 6.00-6.99 | 4.76-4.85 | 6.9-7.0 | 1.71-1.85 | 4.46-4.55 | 11.6-12.0 | 9.25-8.86 | 7.70-8.09 | 47.2-44.66 | 6.00-6.99 | 8-9 | 28-29 | 8.5-8.99 | 120-139 | 165-189 |
| 5.00-5.99 | 4.86+ | 7.1-7.2 | 1.86+ | 4.56+ | 12.1+ | 9.26+ | 8.1+ | 47.3+ | 5.00-5.99 | 7 - | 27 - | 8.49 - | 119 - | 164 - |

FIG. 10B(3)

Football Parameters (Defensive End)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 4.89 - | 6.4 - | 1.4 - | 4.45 - | 10.5 - | 7 - | 6.9 - | 41.54 - | 9.00-10 | 25+ | 31+ | 9.5+ | 180 psi+ | 246+ |
| 8.00-8.99 | 4.90-5.0 | 6.5-6.6 | 1.41-1.55 | 4.46-4.55 | 10.6-11.0 | 7.75-7.01 | 6.91-7.29 | 43.0-41.55 | 8.00-8.99 | 22-24 | 28-30 | 9.9.49 | 160-179 | 220-245 |
| 7.00-8.99 | 5.01-5.1 | 6.7-6.8 | 1.56-1.70 | 4.56-4.65 | 11.1-11.5 | 8.85-7.76 | 7.30-7.69 | 45.2-43.1 | 7.00-8.99 | 20-21 | 26-27 | 8.5-8.99 | 140-159 | 195-219 |
| 6.00-6.99 | 5.11-5.20 | 6.9-7.0 | 1.71-1.85 | 4.66-4.75 | 11.6-12.0 | 9.25-8.86 | 7.70-8.09 | 47.75-45.3 | 6.00-6.99 | 18-19 | 24-25 | 8-8.49 | 120-139 | 170-194 |
| 5.00-5.99 | 5.21+ | 7.1-7.2 | 1.86+ | 4.76+ | 12.1+ | 9.26+ | 8.1+ | 47.76+ | 5.00-5.99 | 17 - | 23 - | 7.99 - | 119 - | 169 - |

FIG. 10B(4)

Football Parameters (Defensive Line)

| Scale | 40 Yard Time | 60 Yard Time | 10 Yard Split | 20 Yard Short Shuttle | 60 Yard Long Shuttle | Compression Force Drive | 3 Cone Drill | Score | Scale | Bench Press | Vertical Jump | Broad Jump | Compression Force Rate | Score |
|---|---|---|---|---|---|---|---|---|---|---|---|---|---|---|
| 9.00-10 | 5.09 - | 6.4 - | 1.4 - | 4.70 - | 10.5 - | 7 - | 6.9 - | 41.99 - | 9.00-10 | 27+ | 29+ | 9.5+ | 180 psi+ | 245+ |
| 8.00-8.99 | 5.10-5.20 | 6.5-6.6 | 1.41-1.55 | 4.71-4.80 | 10.6-11.0 | 7.75-7.01 | 6.91-7.29 | 42.0-43.44 | 8.00-8.99 | 24-26 | 26-28 | 9.9.49 | 160-179 | 220-245 |
| 7.00-8.99 | 5.21-5.30 | 6.7-6.8 | 1.56-1.70 | 4.81-4.90 | 11.1-11.5 | 8.85-7.76 | 7.30-7.69 | 45.65-43.45 | 7.00-8.99 | 22-23 | 24-25 | 8.5-8.99 | 140-159 | 195-219 |
| 6.00-6.99 | 5.31-5.40 | 6.9-7.0 | 1.71-1.85 | 4.91-5.0 | 11.6-12.0 | 9.25-8.86 | 7.70-8.09 | 48.2-45.66 | 6.00-6.99 | 20-21 | 22-23 | 8-8.49 | 120-139 | 170-194 |
| 5.00-5.99 | 5.41+ | 7.1-7.2 | 1.86+ | 5.01+ | 12.1+ | 9.26+ | 8.1+ | 48.3+ | 5.00-5.99 | 19 - | 21 - | 7.99 - | 119 - | 169 - |

FIG. 10B(5)

Football Parameters

| Scale | Long Snap 7 and 15 Yards (Seconds) | 10 Yard Time (Linemen) | 40 Yard Time (Seconds) | 60 Yard Time (Seconds) | Bench Press (Reps) |
|---|---|---|---|---|---|
| 8 | 4 - | 3.9 - | 4.39 - | 6.4 - | 6.4 - |
| 7 | 4.1 | 4 | 4.40-4.50 | 6.5-6.6 | 6.5-6.6 |
| 6 | 4.2 | 4.1 | 4.51-4.70 | 6.7-6.8 | 6.7-6.8 |
| 5 | 4.3 | 4.2 | 4.71-4.90 | 6.9-7.0 | 6.9-7.0 |
| 4 | 4.4 | 4.3 | 4.91-5.10 | 7.1-7.2 | 7.1-7.2 |
| 3 | 4.5 | 4.4 | 5.11-5.30 | 7.3-7.4 | 7.3-7.4 |
| 2 | 4.6+ | 4.5+ | 5.39+ | 7.5+ | 7.5+ |

| Scale | 20 Yard Short Shuttle (Seconds) | Standing Long Jump (Feet) | Vertical Jump (Inches) | 3 Cone Drill (Seconds) | 40 Yard Short Shuttle (Seconds) |
|---|---|---|---|---|---|
| 8 | 4.12 - | 9.0+ | 36+ | 36+ | 36+ |
| 7 | 4.13-4.21 | 8.6-8.9 | 33-35 | 33-35 | 33-35 |
| 6 | 4.22-4.30 | 8.2-8.5 | 30-32 | 30-32 | 30-32 |
| 5 | 4.31-4.39 | 7.8-8.1 | 27-29 | 27-29 | 27-29 |
| 4 | 4.40-4.49 | 7.4-7.7 | 24-26 | 24-26 | 24-26 |
| 3 | 4.50-4.59 | 7.1-7.3 | 21-23 | 21-23 | 21-23 |
| 2 | 5.0+ | 7.0- | 20 - | 20 - | 20 - |

*FIG. 10C*

| Scale | Height | Weight | Wonderlic | Score |
|---|---|---|---|---|
| 9.00-10 | 6'3+ | 215+ | 35-40 | 188+ |
| 8.00-8.99 | 6'1-6'2 | 205-214 | 29-34 | 178-187 |
| 7.00-8.99 | 5'11-6'0 | 195-204 | 23-28 | 170-177 |
| 6.00-6.99 | 5'10-5'9 | 185-194 | 17-22 | 163-169 |
| 5.00-5.99 | 5'8 - | 184 - | 16 - | 155-162 |

*FIG. 10B(6)*

Football Parameters (Offensive Linemen)

| Scale | Long Snap 7 and 15 Yards (Seconds) | 10 Yard Time (Linemen) | 40 Yard Time (Seconds) | 60 Yard Time (Seconds) | Bench Press (Reps) |
|---|---|---|---|---|---|
| 9.00-10 | 4 - | 3.9 - | 4.39 - | 6.4 - | 6.4 - |
| 8.00-8.99 | 4.1 | 4 | 4.40-4.50 | 6.5-6.6 | 6.5-6.6 |
| 7.00-7.99 | 4.2 | 4.1 | 4.51-4.70 | 6.7-6.8 | 6.7-6.8 |
| 6.00-6.99 | 4.3 | 4.2 | 4.71-4.90 | 6.9-7.0 | 6.9-7.0 |
| 5.00-5.99 | 4.4 | 4.3 | 4.91-5.10 | 7.1-7.2 | 7.1-7.2 |
| 3 | 4.5 | 4.4 | 5.11-5.30 | 7.3-7.4 | 7.3-7.4 |
| 2 | 4.6+ | 4.5+ | 5.39+ | 7.5+ | 7.5+ |

| Scale | 20 Yard Short Shuttle (Seconds) | Standing Long Jump (Feet) | Vertical Jump (Inches) | 3 Cone Drill (Seconds) | 40 Yard Short Shuttle (Seconds) |
|---|---|---|---|---|---|
| 8 | 4.12 - | 9.0+ | 36+ | 36+ | 36+ |
| 7 | 4.13-4.21 | 8.6-8.9 | 33-35 | 33-35 | 33-35 |
| 6 | 4.22-4.30 | 8.2-8.5 | 30-32 | 30-32 | 30-32 |
| 5 | 4.31-4.39 | 7.8-8.1 | 27-29 | 27-29 | 27-29 |
| 4 | 4.40-4.49 | 7.4-7.7 | 24-26 | 24-26 | 24-26 |
| 3 | 4.50-4.59 | 7.1-7.3 | 21-23 | 21-23 | 21-23 |
| 2 | 5.0+ | 7.0+ | 20 - | 20 - | 20 - |

FIG. 10D

Football Parameters

| Scale | Long Snap 7 and 15 Yards (Seconds) | 10 Yard Time (Linemen) (Seconds) | 40 Yard Time (Seconds) | 60 Yard Time (Seconds) | Bench Press (Reps) |
|---|---|---|---|---|---|
| 8 | 4 - | 3.9 - | 4.39 - | 6.4 - | 6.4 - |
| 7 | 4.1 | 4 | 4.40-4.50 | 6.5-6.6 | 6.5-6.6 |
| 6 | 4.2 | 4.1 | 4.51-4.70 | 6.7-6.8 | 6.7-6.8 |
| 5 | 4.3 | 4.2 | 4.71-4.90 | 6.9-7.0 | 6.9-7.0 |
| 4 | 4.4 | 4.3 | 4.91-5.10 | 7.1-7.2 | 7.1-7.2 |
| 3 | 4.5 | 4.4 | 5.11-5.30 | 7.3-7.4 | 7.3-7.4 |
| 2 | 4.6+ | 4.5+ | 5.39+ | 7.5+ | 7.5+ |

| Scale | 20 Yard Short Shuttle (Seconds) | Standing Long Jump (Feet) | Vertical Jump (Inches) | 3 Cone Drill (Seconds) | 40 Yard Short Shuttle (Seconds) |
|---|---|---|---|---|---|
| 8 | 4.12 - | 9.0+ | 36+ | 36+ | 36+ |
| 7 | 4.13-4.21 | 8.6-8.9 | 33-35 | 33-35 | 33-35 |
| 6 | 4.22-4.30 | 8.2-8.5 | 30-32 | 30-32 | 30-32 |
| 5 | 4.31-4.39 | 7.8-8.1 | 27-29 | 27-29 | 27-29 |
| 4 | 4.40-4.49 | 7.4-7.7 | 24-26 | 24-26 | 24-26 |
| 3 | 4.50-4.59 | 7.1-7.3 | 21-23 | 21-23 | 21-23 |
| 2 | 5.0+ | 7.0+ | 20 - | 20 - | 20 - |

FIG. 10E

SYSTEM AND METHOD FOR PREDICTING ATHLETIC ABILITY

RELATED APPLICATIONS

This application is a continuation-in-part of co-pending U.S. application Ser. No. 11/702,424 entitled "SYSTEM AND METHOD FOR PREDICTING ATHLETIC ABILITY" filed Feb. 5, 2007.

BACKGROUND

1. Field

Aspects of the invention relate to systems and methods for predicting athletic ability and more particularly to systems and methods which calculate an athletic performance score based upon a plurality of measurements.

2. Discussion of Related Art

Coaches, scouts and agents routinely make decisions about current or prospective players based, at least in part, on a player's athletic ability. Athletic ability is often determined based upon the player's performance in a number of categories relevant to the player's activity. For example, the athletic ability of a baseball pitcher may be determined based on the speed, accuracy, and amount of variety of his pitches, and the athletic ability of a football running back may be determined based upon his speed, agility and strength.

A plurality of athletic parameters are known to help determine athletic ability. For example, a timed run, such as a 60 yard dash is a known athletic parameter for measuring the speed of a player, and the distance a baseball travels after being hit with a bat is another known athletic parameter useful in assessing a batter's athletic ability. The speed of a pitch and the spin on the ball are additional examples of known measurable athletic parameters.

Various devices exist to measure athletic parameters. For example, a stop watch may be used to measure the time it takes for an athlete to run a 60 yard dash and a radar gun may be used to measure the speed of a ball in a baseball game.

Coaches, scouts and agents typically measure a plurality of athletic parameters to help determine an athlete's strengths and weaknesses. Scouts and agents may measure athletic parameters to predict how well an athlete would perform on another team or at a higher level. A scout or coach may travel to a college baseball game or training camp to determine whether or not an athlete would be capable of playing with a professional baseball team. Scouts and coaches are often comparing one athlete to another athlete to predict which athlete has more athletic ability in a particular activity. A variety of athletic parameters are separately measured and the scout or coach makes a subjective determination about the athletic ability of the athlete.

SUMMARY

In one illustrative embodiment, a method for predicting athletic ability is provided. The method includes measuring a first athletic parameter, measuring a second athletic parameter, where the second athletic parameter is different from the first athletic parameter, and calculating a performance score based upon the first athletic parameter and the second athletic parameter, where the performance score is predictive of athletic ability.

In another illustrative embodiment, a system for predicting athletic ability is provided. The system includes at least one device for measuring at least a first athletic parameter and a second athletic parameter, where the second athletic parameter is different from the first athletic parameter. The system further includes a computer for calculating a performance score based upon the first athletic parameter and the second athletic parameter, where the performance score is predictive of athletic ability.

Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which:

FIGS. 5A-5B illustrate examples of pitching performance scores based upon different combinations of baseball athletic parameters;

FIGS. 6A-6B illustrate examples of hitting performance scores based upon different combinations of baseball athletic parameters;

FIGS. 7A-7B illustrate examples of fielding performance scores based upon different combinations of baseball athletic parameters;

FIG. 8 illustrate examples of catching performance scores based upon different combinations of baseball athletic parameters;

FIGS. 9A-9D illustrate examples of running/agility performance scores based upon different combinations of athletic parameters; and FIGS. 10A-10E illustrate examples of performance scores based upon different combinations of football athletic parameters.

DETAILED DESCRIPTION

Figure 1:
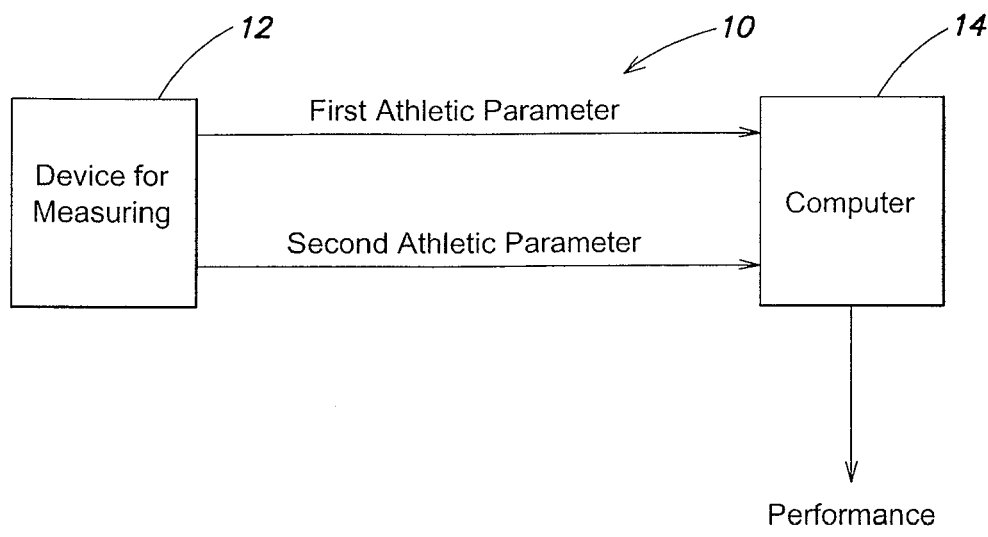
FIG. 1 is a schematic representation of a system for predicting athletic ability according to one illustrative embodiment.

Aspects of the invention are directed to systems and methods for predicting athletic ability. It should be appreciated that the systems and methods may be employed with athletes of all types of activities. For example, the system and method may be used for activities, such as, but not limited to, baseball, football, golf, basketball, lacrosse, soccer, cricket and hockey. It should be appreciated that the system may be configured in any of numerous ways, and that the present invention is not limited to the particular systems described below. Furthermore, it should also be appreciated that the below described methods for predicting athletic ability are not limited to be performed only with the various systems described below.

Applicants recognized that although a number of different athletic parameters may be measured, the ultimate determination of whether or not an athlete met a threshold athletic ability level was always a subjective test. For example, a scout may review numerous measurements of certain athletic parameters for an athlete. These measurements may be individually compared to numerous measurements of other athletes. The scout subjectively predicts which athletes have more athletic ability in comparison to other athletes. Applicants recognized that this process was time consuming and may lead to inaccurate predictions.

Applicants have recognized that obtaining an objective value predictive of athletic ability would be desirable. In particular, Applicants have recognized that an objective value predictive of athletic ability may reduce the likelihood of rendering inaccurate and subjective predictions. In one aspect, therefore, systems and methods for calculating a performance score predictive of athletic ability, based upon a plurality of measurements and/or a combination of measurements is provided. As discussed in greater detail below, for each activity, there are a number of parameters which may be used to assess athletic performance. Aspects of the present invention are directed to methods and systems of utilizing these measurements to assess athletic ability.

The systems and methods described herein may be employed for any suitable purpose, as the present invention is not limited in this regard. In one aspect, the systems and methods may be used by coaches, scouts and/or agents to help determine a player's athletic ability. In another aspect, the systems and methods may be used by the players themselves to objectively determine their performance so that the players can improve their skills.

Turning now to the drawings, it should be appreciated that the drawings illustrate various components and features which may be incorporated into various embodiments of the present invention. For simplification, several drawings may illustrate more than one optional feature or component. However, the present invention is not limited to the specific embodiments disclosed in the drawings. It should be recognized that the present invention encompasses embodiments which may include only a portion of the components illustrated in any one figure, and/or may also encompass embodiments combining components illustrated in multiple different drawings, and/or may also encompass embodiments not explicitly disclosed in the drawings.

In FIG. 1, a schematic representation of a system 10 for predicting athletic ability is shown according to one aspect of the invention. The system 10 includes at least one device 12 for measuring a first athletic parameter and a second athletic parameter. The system 10 also includes a computer 14 which calculates a performance score, based upon the first and second athletic parameters, that is predictive of athletic ability. The various types of devices used to measure athletic parameters are discussed in greater detail below.

Figure 2:
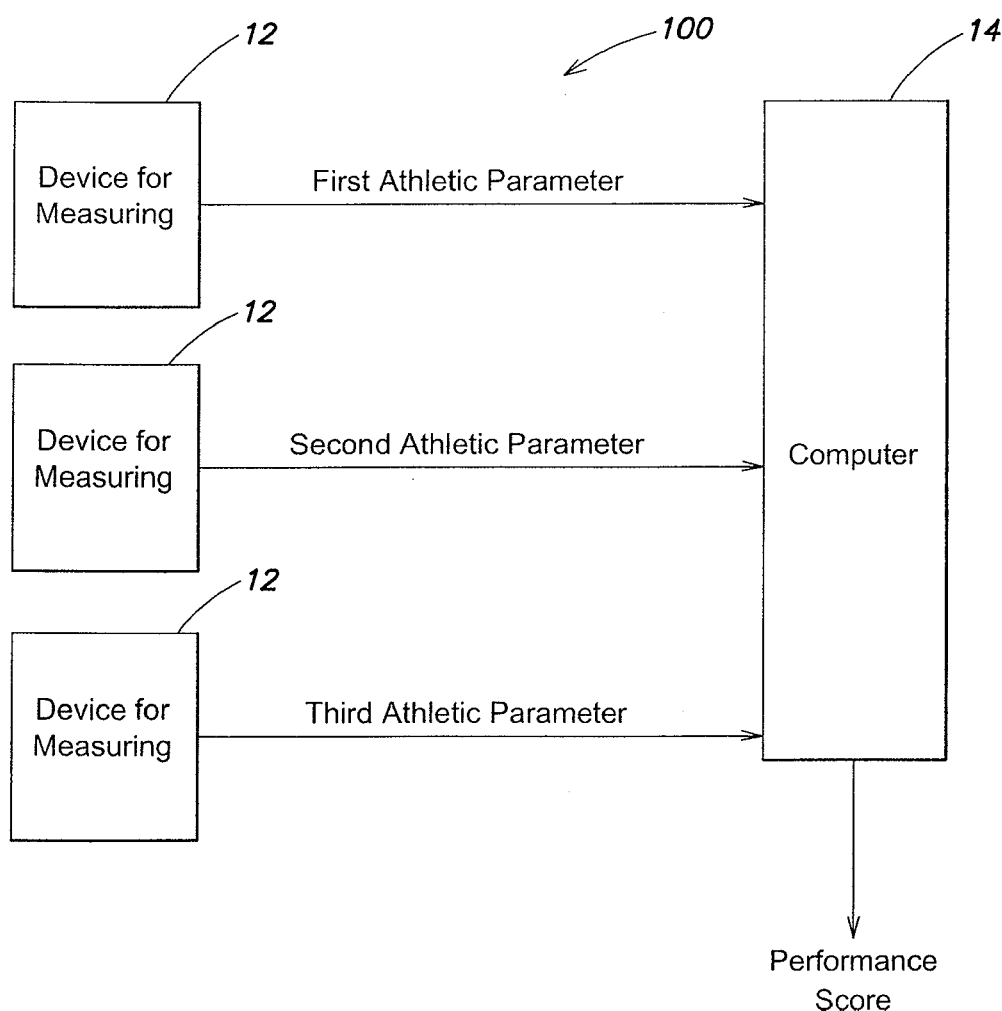
FIG. 2 is a schematic representation of a system for predicting athletic ability according to another illustrative embodiment.

FIG. 2 illustrates another representative system 100 for predicting athletic ability according to another aspect of the invention. The system 100 includes a plurality of devices 12 for measuring athletic parameters. In particular, a first device 12 measures a first athletic parameter, a second device 12 measures a second athletic parameter, and a third device 12 measures a third athletic parameter. A computer 14 calculates a performance score based upon the first, second and third athletic parameters.

Figure 3:
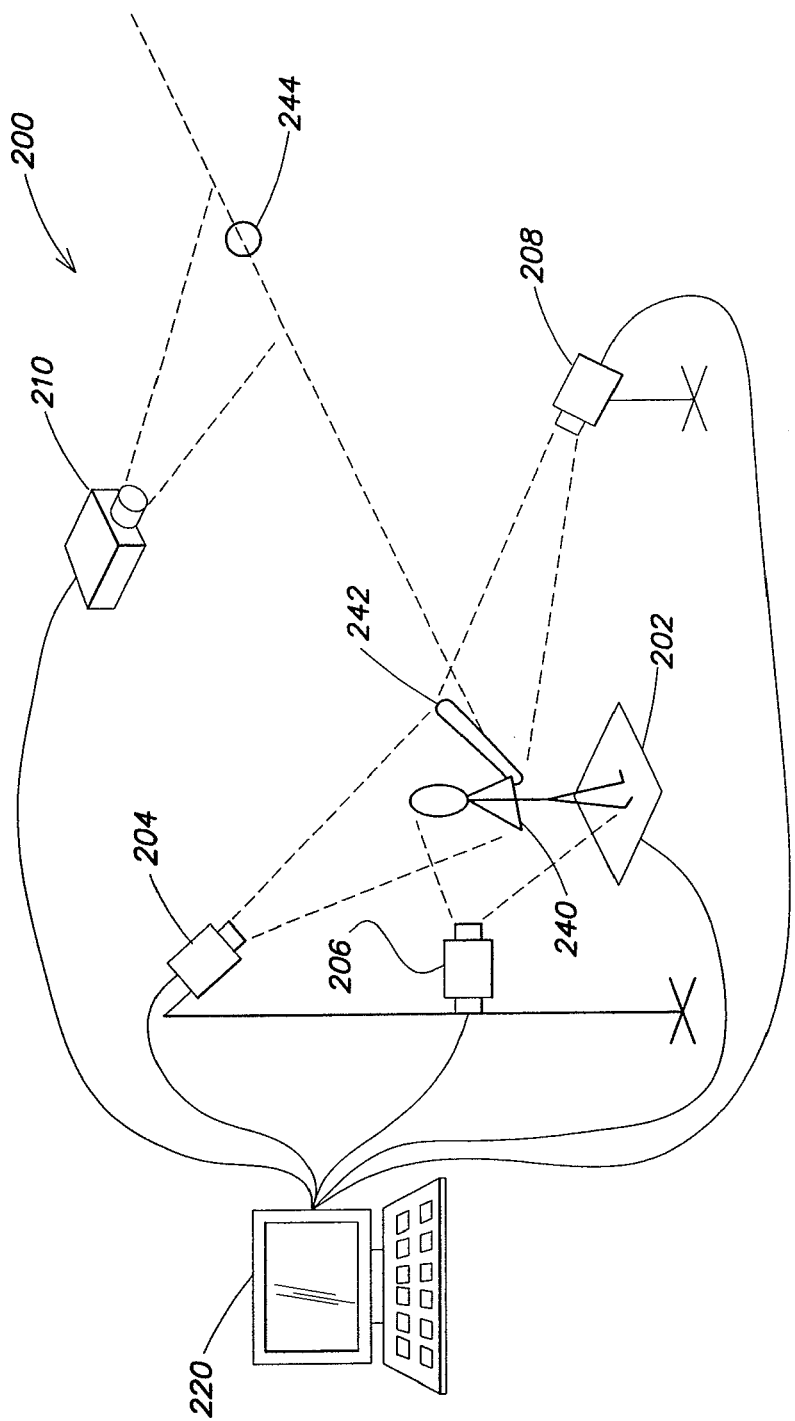
FIG. 3 is a schematic representation of a system for predicting athletic ability according to yet another illustrative embodiment.

One illustrative embodiment of a system 200 for predicting athletic ability in baseball is shown in FIG. 3. The system 200 includes a plurality of devices 202, 204, 206, 208, 210 which measure a plurality of athletic parameters of an athlete 240. These devices, 202, 204, 206, 208, 210 are connected to a computer 220 which calculates a performance score based upon the measured parameters. As shown, the devices connect to the computer 220 with wires. However, it should be appreciated that in other embodiments, the devices connect to a computer wirelessly, and in some embodiments, the computer 220 may be in a location remote from the rest of the system 200. Such a system 200 may be implemented within a baseball park to measure the real time performance of players during an actual baseball game. In other embodiments, the system 200 may be implemented within a practice field for players, coaches, agents and/or scouts to measure a player's athletic performance. As discussed in greater detail below, in yet further embodiments, the system 200 may be incorporated into an indoor or outdoor facility, such as a batting cage.

In the embodiment illustrated in FIG. 3, the athlete 240 is a baseball batter. The devices 202, 204, 206, 208, 210 may be used to measure various parameters of the athlete 240, the bat 242, and/or the ball 244. For example, in one embodiment, the device 202 is a pressure sensor mat. When the athlete 240 stands on the mat, the pressure sensors detect parameters relating to the player's stance, weight distribution and weight shift during his swing. In one embodiment, the other devices 204, 206, 208, 210 are imaging devices which record still shots and/or video of the movement of the athlete 240, the bat 242, and/or the ball 244. In other embodiments, the devices may include other types of sensors, such as, but not limited to, motion sensors, light gate triggers, target sensors, stop watches, radar devices, pitching machines, high speed video cameras, and/or high speed still cameras, as the invention is not so limited. Each device captures data related to an athletic parameter and transmits the data to the computer 220. Further details of devices which may be used to measure various athletic parameters are discussed at greater length below.

As shown in FIG. 3, in one embodiment, all of the devices used to measure athletic parameters are spaced apart from the athlete 240. In other words, the athlete 240 is not wearing any sensing devices 202-210 such that all of the measurements are noninvasive. This allows the system 200 to be portable and easy to use with a plurality of athletes and allows data capture during an actual athletic event, such as a baseball game played by professional baseball players.

In another embodiment, one or more devices used to measure athletic parameters are located directly on the athlete, on the athlete's clothing, and/or on an object held by the athlete.

The computer may use a formula or algorithm to compute the performance score. For example, in one embodiment, a first value is obtained when measuring the first athletic parameter, and a second value is obtained when measuring the second athletic parameter. The computer may input the first and second values into a formula to generate the performance score. The formula may be stored within the computer and it may be preselected by a user operating the system 10, 100. In one embodiment, a performance score may be computed with a formula such as:

$$AX + BY = \text{performance score}$$

According to one embodiment, in the above formula, "X" is the first value obtained when measuring the first athletic parameter and "Y" is the second value obtained when measuring the second athletic parameter. "A" and "B" are multiplying factors which determine the weight of the first and second values. In other words, "A" and "B" determine the weight of the first and second athletic parameters in the formula for determining the performance score. In the above formula, when "A" is greater than "B", the resulting performance score is affected more by the measurement of the first athletic parameter than the measurement of the second athletic parameter.

In another embodiment, a performance score may be computed with a formula such as:

$$AX-BY=\text{performance score}$$

In this formula, "X" and "Y" also refer to the first and second values obtained when measuring the first and second athletic parameters, and "A" and "B" are multiplying factors which determine the weight of the first and second values. In this formula, the second value lowers the performance score. This type of formula may be used when the second athletic parameter is such that the greater the measurement, the lower the athletic ability. A time measurement indicative of speed is one example of an athletic parameter where a greater measured time value for set distance (such as a 40 yard dash) would equate to a slower performance, and thus a lower athletic ability.

As illustrated in FIGS. 2-3, aspects of the invention are directed to systems and methods for predicting athletic ability where more than two athletic parameters are measured. Thus, in another embodiment, the performance score may be computed with a formula such as:

$$AX+BY+CZ+\ldots=\text{performance score}$$

In this formula, a third value is obtained when measuring a third athletic parameter which is shown as "Z", and "C" is the multiplying factor which determines the weight of the third value. In one embodiment, a formula computes the performance value with fourth and fifth athletic parameters, or yet even more parameters, as the invention is not limited in this respect. In some embodiments, the multiplying factors are all positive, in another embodiment, the multiplying factors may all be negative, and in yet another embodiment, the multiplying factors in a formula may include both positive and negative values. It should be recognized that a negative multiplying factor may be used to weight certain athletic parameters where athletic ability is greater the lower the measured value.

In one embodiment, a plurality of formulas are stored in the computer and a user may select which formula is used to compute the performance score. In another embodiment, a user may input their own formula into the computer to compute the performance score. A user-inputted formula may be specifically created to reflect how the user defines athletic ability. In other words, if a measurement of a first athletic parameter is more important to the user than the measurement of a second athletic parameter, the multiplying factor for the first athletic parameter may be larger than the multiplying factor for the second athletic parameter. It should be appreciated that in some embodiments, the computer may include a selection of both stored and user-inputted formulas. In other embodiments, the computer may include one or more complex algorithms which may be used to compute a performance score.

There are a plurality of athletic parameters which may be used in association with the systems and methods for predicting athletic ability according to the present invention. Aspects of the present invention are directed to new systems and/or methods for predicting athletic ability based upon known athletic parameters. Further aspects of the present invention are directed to new systems and/or methods for predicting athletic ability with new athletic parameters which were developed by the Applicants, as will be discussed in more detail below.

Certain embodiments of the present invention are directed to systems and methods where at least the first athletic parameter is directed to movement of an athlete. Examples of such parameters include, but are not limited to movement of an athlete's arms, legs, hands, head, or torso. The athletic parameter may be directed toward measuring an athlete's speed, rotation, stride length, etc. Other embodiments of the present invention are directed to systems and methods where at least the first athletic parameter is directed to movement of an object by an athlete. The object may vary depending upon the specific application and may include a baseball, a soccer ball, a football, a lacrosse ball, a golf ball, hockey puck, etc. The object may be launched by the athlete, as is the case with a golf ball or baseball. In other embodiments, the object may remain in contact with the athlete, as is the case with either a golf club, a baseball bat, hockey stick, or a lacrosse stick.

Figure 4:
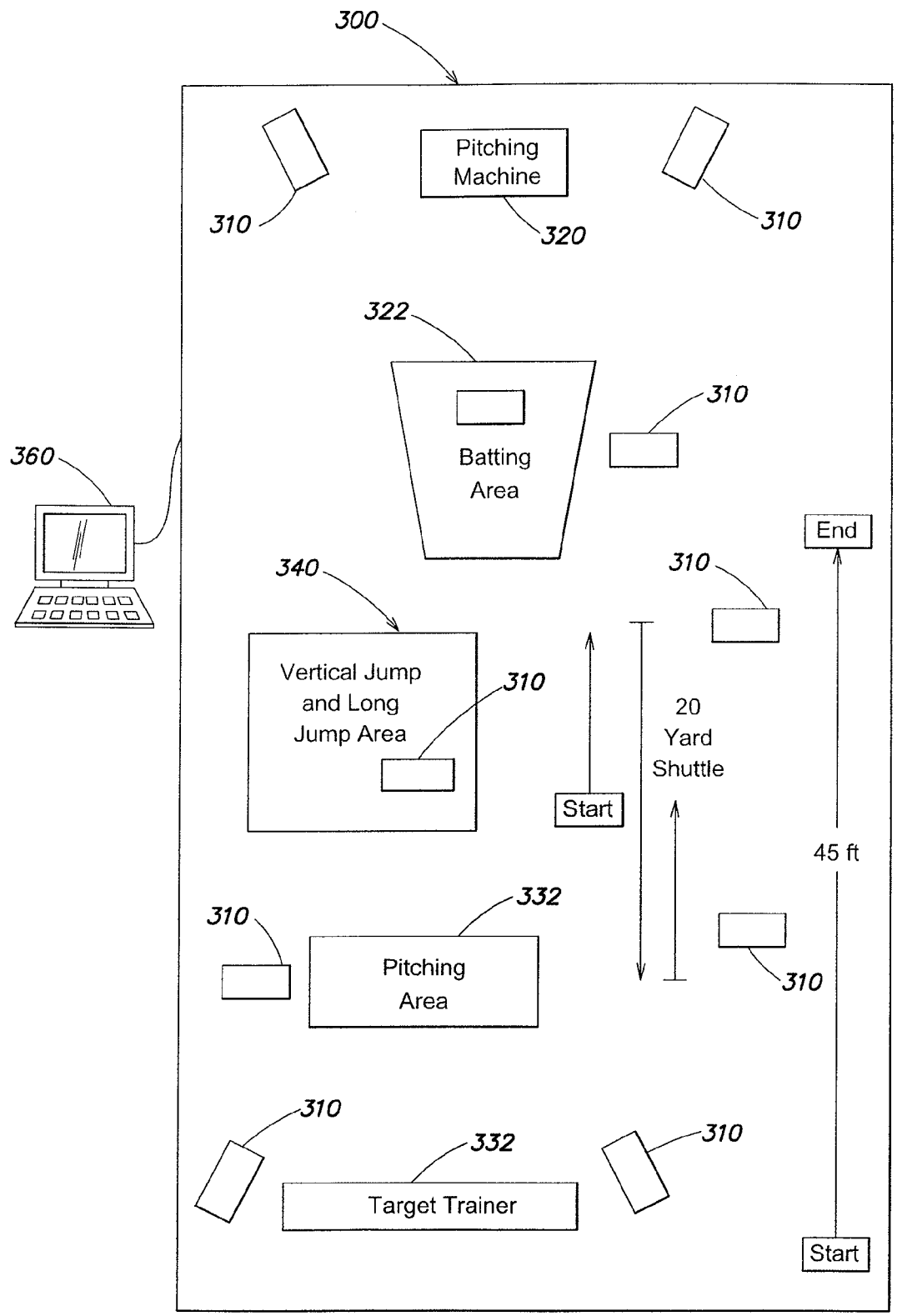
FIG. 4 is a schematic top view of a system for predicting athletic ability according to another illustrative embodiment.

Baseball Athletic Ability:

As discussed above and as shown in FIG. 3, aspects of the present invention are directed to a system 200 for measuring baseball athletic ability. In one embodiment, portions or all of the system is within an indoor or outdoor facility, such as a baseball batting cage. For example, FIG. 4 schematically illustrates a top view of a batting cage system 300 according to one embodiment of the present invention. A plurality of devices 310 are located inside of the batting cage system 300 to measure a plurality of baseball athletic parameters. As shown in FIG. 4, a device 310 is positioned on each side of a pitching machine 320 and also adjacent a batting area 322 to measure various batting athletic parameters. At the other end of the batting cage system 300, a device 310 is positioned adjacent a pitching area 330. Devices 310 are also positioned on each side of a target trainer 332 which may be used to further assess a pitch. Yet another device 310 is positioned in the middle of the batting cage system 300 to measure parameters such as vertical jump and long jump. Other devices 310 may also be in the system 300 to measure timed athletic parameters, such as the 20 yard shuttle and a 45 foot run. These devices 310 collect data for each of the athletic parameters and transmit the data to a computer 360. The computer 360 uses a formula or algorithm to compute a performance score predictive of athletic ability. In one embodiment, the computer 360 is within or near the batting cage system 300. In other embodiments, the computer 360 is remote from the system 300.

In one embodiment, once data is obtained from the devices 310, the data and/or resulting performance scores may be packaged and stored into a database. This information may accumulate in the database to track an individual's improvement over a period of time. In essence, the database may act as a "resume" for athletes, providing objective information regarding athletic ability. In another embodiment, performance scores for a plurality of athletes may be stored in the database. This information may be used to create a scouting report which may be obtained by coaches, scouts, agents and/or players.

It is contemplated that a plurality of batting cage systems 300 may be located throughout the United States, as well as in other parts of the world. These systems 300 may be located at baseball training facilities, and some or all of these systems 300 may interact with a centralized computer 360. A plurality of systems 300 may interact together forming a network which may be accessible from a variety of geographic locations. Athletes of all levels and abilities may come to these facilities to use the system 300. The athletes may be charged for the evaluation. Potential customers for such a system includes the individual players, colleges and universities, and professional leagues, such as Major League Baseball (MLB). Potential customers, such as the MLB, may subscribe to a service allowing them to download an athlete's information from a centralized computer 360.

In one embodiment, the batting cage system 300 is approximately 72 feet long, 15 feet wide and 12 feet high. However, it should be appreciated that in other embodiments, the dimensions of the system may vary depending upon the athletic parameters being measured. Furthermore, although the above-described system 300 is directed to baseball athletic parameters, the invention is not limited in this respect. Other embodiments are directed to systems for predicting athletic ability in other activities, such as, but not limited to football, hockey, lacrosse golf, basketball, soccer and cricket. For example, instead of a batting area 322 and pitching machine 320, the system 300 may include a golf club swinging area if the system was directed to predicting golf athletic ability.

Turning now to FIG. 5A-5B, examples of baseball pitching performance scores based upon different combinations of baseball athletic parameters are illustrated. It should be appreciated that the invention is not limited only to the specific combinations of athletic parameters shown in the figures. FIGS. 5A-5B provide representative combinations for predicting athletic ability of a pitcher. It should also be recognized that different formulas and/or different combinations of athletic parameters would result in different resulting performance values.

There are many different pitching athletic parameters which may be measured, resulting in numerous combinations. FIGS. 5A-5B illustrates several combinations of athletic parameters for various types of pitches, including two seam fast balls, four seam fast balls, curve balls, change up pitches, sliders, and splitters. Although not illustrated in FIGS. 5A-5B, it should be appreciated that other types of pitches may also be analyzed, as the present invention is not limited in this respect.

The following table provides an exemplary list of athletic parameters to measure the athletic ability of a pitcher. FIGS. 5A-5B illustrates examples of resulting performance scores for different combinations of the following athletic parameters.

| Pitching Athletic Parameters | |
|---|---|
| Athletic Parameter | Description |
| Ball Speed | Speed of the ball may be measured in miles per hour (MPH) and may be measured at release, at a midpoint, and/or at home plate. |
| Movement | Movement of the ball during the pitch from a plane. The plane may be within eight feet from home plate. The movement may be left, right, up or down, and may be measured in inches. |
| Break Angle | Break angle is a measure of the angle of the ball movement at a specific distance, such as eight feet away from home plate, and break angle is often measured in degrees. |
| Accuracy | Accuracy of a pitch may be defined as the ratio of balls that pass through a specific area or volume. In one embodiment, accuracy may be based upon the number of strikes to balls. |
| Fast Ball Differential | Fast ball differential is the speed difference between a player's fast ball pitch and a change-up pitch. The fast ball differential is measured in MPH and may be used to evaluate the strength of a change-up pitch. |

| Pitching Athletic Parameters | |
|---|---|
| Athletic Parameter | Description |
| Deceptive Visibility Factor (DVF) | Deceptive visibility factor is defined as the amount of time that the ball is hidden from the hitter and it is often measured in seconds. |
| Spin Rate | Spin rate is a measure of the rotation of the ball during the pitch. |
| Spin Axis | Spin axis is a measure of the axis of rotation of the ball. |
| Flight Time | Flight time is a measure of the amount of time the ball is in flight and it is often measured in milliseconds. |
| Flight Time After Break Angle or Movement | Flight time after break angle or movement is a measure of the amount of time the ball is in flight after the ball starts to break or after the greatest degree of movement or swerve of the ball, and it is often measured in milliseconds. |
| Release Height/Location | Release Height/Location is a measure of the relative height and position that a ball is released from the pitcher. The height may be relative to ground and the location may be the horizontal position relative to the center of the mound. An example would be Release 4'2" from ground @ 2'8" right from center of pitching mound. This may be shown in a scatter chart. |
| Stride Length | Stride length measures how far apart the pitcher's feet are while pitching. |
| Arm Angle | Arm angle is a measure of the angle of the pitcher's arm when the ball is released and is typically measured in degrees. |
| Delivery time or Tempo time | Tempo is a measure of the amount of time it takes for a pitcher to throw a pitch. Tempo may be measured in seconds and is measured from when the pitcher lifts his foot up and down until release of the ball. |
| Distance at Release | Distance at release is defined as the distance the ball travels from the pitch to home plate. In a conventional field, where the pitching mound is 60 feet away from home plate, the distance to release parameter is equal to 60 feet minus the length that the arm extends past the pitching mound at the moment the ball is released. |
| Separation to Release | Separation to Release is a time measurement from a "set position" (i.e. with both hands together) to a separation in order to throw the ball, to slot position (arm angle), to release of the ball. |

As discussed above, the resulting performance score is based upon a plurality of athletic parameters and is predictive of athletic ability. For example, as illustrated at the top of FIG. 5A, a pitcher who throws a four seam fastball with an accuracy of 85%, an average speed of 93 MPH, with ball movement of 5 inches may have a resulting performance score of 183. Another pitcher who throws a four seam fastball with an accuracy of 70%, an average speed of 85 MPH, with ball movement of 2 inches may have a resulting performance score of 157. In this particular embodiment, the formula used to compute the performance value may be defined as:

$$1X+1Y+1Z=\text{performance score}$$

In the above formula, "X" is the value of the accuracy, "Y" is the value of the ball speed, and "Z" is the value of the movement of the fast ball pitch. For simplicity, in the above formula, the multiplying factor which determines the weight of the three measured values is equal to 1. It should be appreciated that in other embodiments, the multiplying factor may vary as the invention is not limited to a particular formula for determining a performance score. For example, in one embodiment, the multiplying factor for the ball speed may be 3 and the multiplying factor for accuracy may be 4 in a formula where accuracy is more important than speed.

In certain embodiments, a threshold performance score is set by a scout and an athlete must obtain at least that threshold score to be further considered by the scout. In other embodiments, a coach may set goal performance scores for his/her players. This goal may be set at the end of a season for a player to achieve during the off season. In further embodiments, a player may use the system to track his/her individual improvement each year.

In one embodiment, the resulting performance score may be scaled into a different format. In one embodiment, the performance score may be scaled to the conventional 20-80 Major League Baseball (MLB) scale. Unlike the conventional MLB scale which scales only one athletic parameter, the present invention may use the MLB scale to scale a resulting performance score which is based on a plurality of athletic parameters. FIGS. 5A-5B illustrate columns labeled "Scale" which correspond to the MLB scale. As shown in FIG. 5A, in the above described embodiment, the pitcher with a resulting performance score of 183 has a scaled score of 70, and the pitcher with a resulting performance score of 157 has a scaled score of 40. In another embodiment, the performance score may be scaled to a score between 2 and 8. It should be appreciated that in other embodiments, the performance score may be scaled to other formats, as the present invention is not so limited.

As discussed above, FIGS. 5A-5B provide representative combinations for predicting athletic ability of a pitcher. It should be recognized that other combinations of athletic parameters are contemplated, as the present invention is not limited in this respect. The following list provides additional exemplary combinations of athletic parameters which may be used to predict athletic ability of a pitcher.

Additional Pitching Combinations

MPH (FROM RELEASE, MIDPOINT, OR AT PLATE)+MOVEMENT
MPH (FROM RELEASE, MIDPOINT, OR AT PLATE)+BREAK ANGLES
MPH (FROM RELEASE, MIDPOINT, OR AT PLATE)+ACCURACY
MPH (FROM RELEASE, MIDPOINT, OR AT PLATE)+SPIN RATE
MPH (FROM RELEASE, MIDPOINT, OR AT PLATE)+SPIN AXIS
MPH (FROM RELEASE, MIDPOINT, OR AT PLATE)+FLIGHT TIME
MPH (FROM RELEASE, MIDPOINT, OR AT PLATE)+RELEASE HEIGHT/LOCATION
TEMPO TIME+DECEPTIVE VISIBILITY FACTOR (DVF)
SEPARATION TO RELEASE+DECEPTIVE VISIBILITY FACTOR (DVF)
MOVEMENT+BREAK ANGLES
MOVEMENT+SPIN RATE
MOVEMENT+SPIN AXIS
MOVEMENT+FLIGHT TIME
MOVEMENT+RELEASE HEIGHT/LOCATION
FASTBALL DIFFERENTIALS+MPH (FROM RELEASE, MIDPOINT, OR AT PLATE)
FASTBALL DIFFERENTIALS+MOVEMENT
FASTBALL DIFFERENTIALS+BREAK ANGLES
BREAK ANGLES+SPIN RATE
BREAK ANGLES+SPIN AXIS
BREAK ANGLES+FLIGHT TIME
BREAK ANGLES+RELEASE HEIGHT/LOCATION
MOVEMENT+ACCURACY
BREAK ANGLES+ACCURACY
SPIN RATE+ACCURACY
SPIN RATE+SPIN AXIS
SPIN RATE+FLIGHT TIME
SPIN RATE+RELEASE HEIGHT/LOCATION
SPIN AXIS+FLIGHT TIME
SPIN AXIS+RELEASE HEIGHT/LOCATION
TOTAL FLIGHT TIME OF PITCH+FLIGHT TIME AFTER ANY BREAK ANGLE OR MOVEMENT
MPH (FROM RELEASE, MIDPOINT, OR AT PLATE)+MOVEMENT+BREAK ANGLE
MPH (FROM RELEASE, MIDPOINT, OR AT PLATE)+MOVEMENT+ACCURACY
MPH (FROM RELEASE, MIDPOINT, OR AT PLATE)+BREAK ANGLES+ACCURACY
MPH (FROM RELEASE, MIDPOINT, OR AT PLATE)+SEPARATION TO RELEASE+TEMPO TIME
MPH (FROM RELEASE, MIDPOINT, OR AT PLATE)+TEMPO TIME+MOVEMENT
MPH (FROM RELEASE, MIDPOINT, OR AT PLATE)+SEPARATION TO RELEASE+MOVEMENT
MPH (FROM RELEASE, MIDPOINT, OR AT PLATE)+SEPARATION TO RELEASE+BREAK ANGLES
MPH (FROM RELEASE, MIDPOINT, OR AT PLATE)+SEPARATION TO RELEASE+ACCURACY
MPH (FROM RELEASE, MIDPOINT, OR AT PLATE)+TEMPO TIME+BREAK ANGLES
MPH (FROM RELEASE, MIDPOINT, OR AT PLATE)+TEMPO TIME+ACCURACY
MOVEMENT+BREAK ANGLES+TEMPO TIME
MOVEMENT+BREAK ANGLES+SEPARATION TO RELEASE
MOVEMENT+TEMPO TIME+ACCURACY
MOVEMENT+SEPARATION TO RELEASE+ACCURACY
MOVEMENT+SEPARATION TO RELEASE+TEMPO TIME
MOVEMENT+BREAK ANGLES+ACCURACY
BREAK ANGLES+SEPARATION TO RELEASE+TEMPO TIME
BREAK ANGLES+ACCURACY+TEMPO TIME
BREAK ANGLES+ACCURACY+SEPARATION TO RELEASE
SEPARATION TO RELEASE+TEMPO TIME+ACCURACY
SEPARATION TO RELEASE+TEMPO TIME+DECEPTIVE VISIBILITY FACTOR (DVF)

The system and method of predicting athletic ability is also applicable to other types of athletic parameters, in addition to pitching. The following table provides an exemplary list of athletic parameters to measure athletic ability of a baseball hitter. FIGS. 6A-6B illustrate examples of resulting performance score for some of the different combinations of the hitting athletic parameters described below.

| Hitting Athletic Parameters | |
| --- | --- |
| Athletic Parameter | Description |
| Bat Speed | Bat speed is the speed of the bat when swung across home plate and is typically measured in miles per hour (MPH). |
| Distance | This is the distance from home plate the ball travels after hit which is typically measured in feet. |

-continued

Hitting Athletic Parameters

| Athletic Parameter | Description |
|---|---|
| Ball Velocity off Bat | Ball velocity is the speed of the ball after hit with the bat, typically measured MPH. |
| Barrel Accuracy or Sweet Spot Contact | This is the percentage of time the player hits the ball on the sweet spot of the bat. |
| Barrel Angle at Contact % | Barrel angle is the angle of the bat when the bat contacts the ball. A percentage may be calculated by determining where the ball should be hit based on the location of the pitch (i.e. Right handed batter, outside pitch should be hit to right field or right of center). |
| Arm Strength | Arm strength is a measure of the speed of the player's arm when swinging. This is typically measured in MPH. |
| Range (Left) | This is a measure of the time in seconds it takes to move 5 yards to the left. |
| Range (Right) | This is a measure of the time in seconds in takes to move 5 yards to the right. |
| Reaction Time | Reaction time is a timed measure of a batter's ability to recognize the speed, spin and location of a ball as it nears the hitting zone. |
| Swing Path | This is a measure of the path and angle of approach of the bat swing. Launch angle to contact, to extension, and to follow through may be obtained based upon the Swing Path. |
| Stride Length | The length of a hitter's stride, which may be measured in feet. |
| Weight Shift | This is the weight distribution throughout a batter's swing which may be measured by a pressure sensor. |
| Hip Rotation at Contact | This is the amount of hip rotation of the player at the moment the player's bat makes contact with the ball which may be measured in degrees. |
| Vertical Launch Angle | Vertical launch angle is the initial elevation angle of the ball with respect to the ground immediately after impact with bat. |
| Horizontal Launch Angle | Horizontal launch angle is the angle at which the ball leaves the bat. |
| Spin Rate | Spin rate is a measure of the rotation of the batted ball. |
| Spin Axis | Spin axis is the axis of rotation of the batted ball, which may be split up into two components (sidespin and backspin). |
| Ball Compression Rate | Ball compression rate is a measure of how much the ball is distorted (flattens) upon impact with the bat. |

As shown at the top of FIG. 6A, in one example, a hitter that has a bat speed of 95 MPH, hitting an average distance of 425 feet, with a ball velocity of 125 MPH, a barrel accuracy of 98%, and a barrel angle at contact percent of 98% has a resulting performance score of 841. In contrast, a hitter that has a bat speed of 70 MPH, hitting an average distance of 300 feet, with a ball velocity of 75 MPH, a barrel accuracy of 83%, and a barrel angle at contact percent of 83% has a resulting performance score of 611. In this particular embodiment, the formula used to compute the performance value may be defined as:

$$1V+1W+1X+1Y+1Z=\text{performance score}$$

In the above formula, "V" is the value of the bat speed, "W" is the value for the average distance, "X" is the value of the ball velocity, "Y" is the value of the barrel accuracy, and "Z" is the value of the barrel angle at contact percent. For simplicity, in the above formula, the multiplying factor which determines the weight of the five measured values is equal to 1. It should be appreciated that in other embodiments, the multiplying factor may vary as the invention is not limited to a particular formula. It should be recognized that other combinations of hitting athletic parameters not shown in the figures may be measured to calculate a performance score according to the present invention.

As discussed above, FIGS. 6A-6B provide representative combinations for predicting athletic ability of a baseball hitter. It should be recognized that other combinations of athletic parameters may also be used to predict athletic ability, as the present invention is not limited in this respect. The following list provides additional exemplary combinations of athletic parameters which may be used to predict athletic ability of a baseball hitter.

Additional Hitting Combinations

BAT SPEED+DISTANCE
BAT SPEED+BALL SPEED/VELOCITY
BAT SPEED+BARREL ACCURACY
BAT SPEED+BARREL ANGLE
BAT SPEED+ARM STRENGTH
BAT SPEED+GLOVE TO RELEASE
BAT SPEED+RANGE
BAT SPEED+THROWING ACCURACY
BAT SPEED+VERTICAL LAUNCH ANGLE
BAT SPEED+HORIZONTAL LAUNCH ANGLE
BAT SPEED+SPIN RATE
BAT SPEED+SPIN AXIS
BAT SPEED+BALL COMPRESSION RATE
DISTANCE+BALL SPEED/VELOCITY
DISTANCE+BARREL ACCURACY
DISTANCE+BARREL ANGLE
DISTANCE+ARM STRENGTH
DISTANCE+THROWING ACCURACY
DISTANCE+GLOVE TO RELEASE
DISTANCE+RANGE
DISTANCE+VERTICAL LAUNCH ANGLE
DISTANCE+HORIZONTAL LAUNCH ANGLE
DISTANCE+SPIN RATE
DISTANCE+SPIN AXIS
DISTANCE+BALL COMPRESSION RATE
BALL SPEED/VELOCITY+BARREL ACCURACY
BALL SPEED/VELOCITY+ARM STRENGTH
BALL SPEED/VELOCITY+THROWING ACCURACY
BALL SPEED/VELOCITY+BARREL ANGLE
BALL SPEED/VELOCITY+GLOVE TO RELEASE
BALL SPEED/VELOCITY+RANGE
BALL SPEED/VELOCITY+VERTICAL LAUNCH ANGLE
BALL SPEED/VELOCITY+HORIZONTAL LAUNCH ANGLE
BALL SPEED/VELOCITY+SPIN RATE
BALL SPEED SPIN AXIS
BALL SPEED+BALL COMPRESSION RATE
BARREL ACCURACY+ARM STRENGTH
BARREL ACCURACY+RANGE
BARREL ACCURACY+GLOVE TO RELEASE
BARREL ACCURACY+THROWING ACCURACY
BARREL ACCURACY+BARREL ANGLE
BARREL ACCURACY+VERTICAL LAUNCH ANGLE
BARREL ACCURACY+HORIZONTAL LAUNCH ANGLE
BARREL ACCURACY+SPIN RATE
BARREL ACCURACY+SPIN AXIS
BARREL ACCURACY+BALL COMPRESSION RATE
SPIN RATE+SPIN AXIS
SPIN RATE+BALL COMPRESSION RATE
SPIN RATE+HORIZONTAL LAUNCH ANGLE

SPIN RATE+VERTICAL LAUNCH ANGLE
SPIN AXIS+VERTICAL LAUNCH ANGLE
SPIN AXIS+HORIZONTAL LAUNCH ANGLE
SPIN AXIS+BALL COMPRESSION RATE
BAT SPEED+DISTANCE+BALL SPEED/VELOCITY
BAT SPEED+DISTANCE+BARREL ACCURACY
BAT SPEED+DISTANCE+BARREL ANGLE
BAT SPEED+BALL SPEED/VELOCITY+BARREL ACCURACY
BAT SPEED+BALL SPEED/VELOCITY+BARREL ANGLE
BAT SPEED+DISTANCE+ARM STRENGTH
BAT SPEED+BALL SPEED/VELOCITY+ARM STRENGTH
BAT SPEED+BARREL ACCURACY+ARM STRENGTH
BAT SPEED+BARREL ACCURACY+BARREL ANGLE
BAT SPEED+ARM STRENGTH+GLOVE TO RELEASE
BAT SPEED+ARM STRENGTH+RANGE
BAT SPEED+ARM STRENGTH+THROWING ACCURACY
BAT SPEED+THROWING ACCURACY+RANGE
BAT SPEED+THROWING ACCURACY+GLOVE TO RELEASE
BAT SPEED+GLOVE TO RELEASE+RANGE
BAT SPEED+GLOVE TO RELEASE+ACCURACY
BAT SPEED+GLOVE TO RELEASE+BARREL ACCURACY
BAT SPEED+GLOVE TO RELEASE+BARREL ANGLE
BAT SPEED+BALL SPEED/VELOCITY+RANGE
BAT SPEED+BALL SPEED/VELOCITY+GLOVE TO RELEASE
BAT SPEED+BALL SPEED/VELOCITY+THROWING ACCURACY
BAT SPEED+DISTANCE+GLOVE TO RELEASE
BAT SPEED+DISTANCE+THROWING ACCURACY
BAT SPEED+DISTANCE+RANGE
BALL SPEED/VELOCITY+RANGE+GLOVE TO RELEASE
BALL SPEED/VELOCITY+RANGE+THROWING ACCURACY
BALL SPEED/VELOCITY+GLOVE TO RELEASE+BARREL ACCURACY
BALL SPEED/VELOCITY+GLOVE TO RELEASE+BARREL ANGLE
BALL SPEED/VELOCITY+GLOVE TO RELEASE+THROWING ACCURACY
BALL/SPEED/VELOCITY+DISTANCE+ARM STRENGTH
BALL/SPEED/VELOCITY+DISTANCE+THROWING ACCURACY
BALL/SPEED/VELOCITY+DISTANCE+RANGE
BALL/SPEED/VELOCITY+DISTANCE+GLOVE TO RELEASE
BALL/SPEED/VELOCITY+DISTANCE+BARREL ACCURACY
BALL/SPEED/VELOCITY+DISTANCE+BARREL ANGLE
BALL SPEED/VELOCITY+ARM STRENGTH+ACCURACY
BALL SPEED/VELOCITY+ARM STRENGTH+GLOVE TO RELEASE
BALL SPEED/VELOCITY+ARM STRENGTH+RANGE
BALL SPEED/VELOCITY+ARM STRENGTH+BARREL ANGLE
BALL SPEED/VELOCITY+ARM STRENGTH+BARREL ACCURACY
BALL SPEED/VELOCITY+RANGE+BARREL ACCURACY
BALL SPEED/VELOCITY+RANGE+BARREL ANGLE
DISTANCE+BARREL ACCURACY+BARREL ANGLE
DISTANCE+BARREL ACCURACY+ARM STRENGTH
DISTANCE+BARREL ACCURACY+GLOVE TO RELEASE
DISTANCE+BARREL ACCURACY+RANGE
DISTANCE+BARREL ACCURACY+THROWING ACCURACY
DISTANCE+ARM STRENGTH+BARREL ANGLE
DISTANCE+ARM STRENGTH+GLOVE TO RELEASE
DISTANCE+ARM STRENGTH+RANGE
DISTANCE+ARM STRENGTH+THROWING ACCURACY
BARREL ANGLE+RANGE+BARREL ACCURACY

Aspects of the present invention are also directed to predicting the athletic ability of a baseball fielder. FIGS. 7A-7B illustrate examples of resulting performance scores for some of the different combinations of fielding athletic parameters. The following table provides an exemplary list of athletic parameters to measure athletic ability of a baseball fielder, some of which are illustrated in FIGS. 7A-7B.

| Fielding Athletic Parameters | |
|---|---|
| Athletic Parameter | Description |
| Glove to Release | Glove to release is a measure of the elapsed time from when the ball hits a fielder's glove to when the fielder releases the ball (i.e. fielding a ground ball with a throw). This is typically measured in seconds. |
| Arm Strength | Arm strength is a measure of the speed of the fielder's arm after the arm passes the head. This is typically measured in MPH. |
| Throwing Accuracy | Throwing accuracy is equal to the percentage that the fielder throws a ball that hits a particular target. |
| Range (Left) | This is a measure of the time in seconds it takes to move 5 yards to the left. |
| Range (Right) | This is a measure of the time in seconds it takes to move 5 yards to the right. |
| Arm Angle at Release | This is a measure of the angle of the fielder's arm when the fielder releases the ball. This may be measured in degrees. |
| Transfer Time | Transfer time is a measure of the elapsed time from standing up and taking a throw (i.e. Infield Double Play) This may be measured in seconds. |
| Release Height/Location | Release Height/Location is a measure of the relative height and position that a ball is released from the fielder. The height may be relative to ground and the location may be the horizontal position relative to the center of the fielder's body. An example would be Release 3'4" from ground @ 3'2" right from center of fielder's body. This may be shown in a scatter chart. |

FIGS. 7A-7B provide representative combinations for predicting athletic ability of a baseball fielder. It should be recognized that other combinations of athletic parameters may be used to determine athletic ability of a fielder, as the present invention is not limited in this respect. Additional exemplary combinations of athletic parameters which may be used to predict athletic ability of a baseball fielder are provided in the following list.

Additional Fielding Combinations

ARM STRENGTH/MPH+THROWING ACCURACY
ARM STRENGTH/MPH+GLOVE TO RELEASE
ARM STRENGTH/MPH+RANGE
ARM STRENGTH/MPH+TRANSFER TIME
ARM STRENGTH/MPH+RELEASE HEIGHT/LOCATION
GLOVE TO RELEASE+THROWING ACCURACY
GLOVE TO RELEASE+RANGE
GLOVE TO RELEASE+RELEASE HEIGHT/LOCATION
RANGE+THROWING ACCURACY
ARM STRENGTH/MPH+GLOVE TO RELEASE+ THROWING ACCURACY
ARM STRENGTH/MPH+GLOVE TO RELEASE+ RANGE
ARM STRENGTH/MPH+THROWING ACCURACY+ RANGE
GLOVE TO RELEASE+THROWING ACCURACY+ RANGE

Turning to FIG. 8, examples of performance scores for representative combinations of baseball catching athletic parameters are illustrated. The following table provides an exemplary list of athletic parameters to measure athletic ability of a baseball catcher, some of which are illustrated in FIG. 8.

Catching Athletic Parameters

| Athletic Parameter | Description |
| --- | --- |
| Glove to Release | Glove to release is a measure of the elapsed time from when the ball hits a catcher's glove to when the catcher releases the ball. This is typically measured in seconds. |
| Arm Strength | Arm strength is a measure of the speed of the catcher's arm after the arm passes the head. This is typically measured in MPH. |
| Throwing Accuracy | Throwing accuracy is equal to the percentage that the catcher throws a ball that hits a particular target. |
| Range (Left) | This is a measure of the time in seconds it takes to move 5 yards to the left. |
| Range (Right) | This is a measure of the time in seconds it takes to move 5 yards to the right. |
| Arm Angle at Release | This is a measure of the angle of the catcher's arm when the catcher releases the ball. This may be measured in degrees. |
| Pop Times Home to Second Base | This is the elapsed time from catcher's glove to second base which may be measured in seconds. |
| Release Height/Location | Release Height/Location is a measure of the relative height and position that a ball is released from the catcher. The height may be relative to ground and the location may be the horizontal position relative to the center of the catcher's body. This may be shown in a scatter chart. |

FIG. 8 provide representative combinations for predicting athletic ability of a baseball catcher. It should be recognized that other combinations of athletic parameters may be used to determine athletic ability of a catcher, as the present invention is not limited in this respect. Additional exemplary combinations of athletic parameters which may be used to predict athletic ability of a baseball catcher are provided in the following list.

Additional Catching Combinations

ARM STRENGTH/MPH+GLOVE TO RELEASE
ARM STRENGTH/MPH+THROWING ACCURACY
ARM STRENGTH/MPH+RANGE
ARM STRENGTH/MPH+RELEASE HEIGHT/LOCATION
GLOVE TO RELEASE+THROWING ACCURACY
GLOVE TO RELEASE+RANGE
GLOVE TO RELEASE+RELEASE HEIGHT/LOCATION
ARM STRENGTH/MPH+GLOVE TO RELEASE+ THROWING ACCURACY
ARM STRENGTH/MPH+GLOVE TO RELEASE+ RANGE
ARM STRENGTH/MPH+THROWING ACCURACY+ RANGE
GLOVE TO RELEASE+THROWING ACCURACY+ RANGE

FIG. 9A-9D illustrates examples of performance scores which include representative combinations of running and agility athletic parameters. Although some of these parameters are designed specifically to gauge the athletic ability of a baseball player, it should be appreciated that many of these parameters may also be used for athletes who participate in other activities, as the invention is not so limited. Furthermore, the example performance scores in FIGS. 9A-9D also illustrate combinations of both running or agility athletic parameters along with other parameters, such as pitching, fielding, and hitting athletic parameters described above. It should be appreciated that aspects of the present invention are directed to calculating performance scores to assess athletic ability based upon numerous combinations of athletic parameters which may include one or more pitching, hitting, fielding, catching, running and/or agility parameters. The following table provides an exemplary list of running and agility athletic parameters, some of which are illustrated in FIGS. 9A-9D.

Running & Agility Athletic Parameters

| Athletic Parameter | Description |
| --- | --- |
| Home to First | This is typically a 90 foot sprint from home base to first base, measured in seconds. |
| Vertical Jump | This is a measure of jumping ability, measured in vertical feet or inches. |
| Standing Long Jump (Broad Jump) | This is a measure of jumping ability, measured in horizontal feet. |
| 40 Yard Dash | A 40 yard sprint, measured in seconds. |
| 60 Yard Dash | A 60 yard sprint, measured in seconds. |
| Acceleration | Acceleration may be measured with a 10 yard sprint, measured in seconds from a stopped position to a full stride. |
| Frequency of Steps | This is a measure of the number of steps in a certain sprint. |
| Length of Stride | This is the stride length in a certain sprint. |
| 20 Yard Shuttle | The 20 Yard Shuttle is a short sprint to gauge agility, starting 5 yards to the left, 10 yards to the right, then 5 yards to the left. |

FIGS. 9A-9D provide representative combinations for predicting athletic ability. It should be recognized that other combinations of athletic parameters may be used to determine athletic ability. Additional exemplary combinations of athletic parameters which may be used to predict running and agility athletic ability are provided in the following list.

Additional Running & Agility Combinations

60 YARD+ARM STRENGTH
60 YARD+BAT SPEED
60 YARD+BALL SPEED/VELOCITY
60 YARD+DISTANCE
60 YARD+BARREL ACCURACY
60 YARD+BARREL ANGLE
60 YARD+GLOVE TO RELEASE
60 YARD+RANGE
60 YARD+THROWING ACCURACY
60 YARD+VERTICAL JUMP
60 YARD+BROAD JUMP
60 YARD+90 FEET
60 YARD+10 YARD SPLIT
90 FEET+ARM STRENGTH
90 FEET+BAT SPEED
90 FEET+BALL SPEED/VELOCITY
90 FEET+DISTANCE
90 FEET+BARREL ACCURACY
90 FEET+BARREL ANGLE
90 FEET+GLOVE TO RELEASE
90 FEET+RANGE
90 FEET+THROWING ACCURACY
90 FEET+VERTICAL JUMP
90 FEET+BROAD JUMP
90 FEET+10 YARD SPLIT
10 YARD SPLIT+ARM STRENGTH
10 YARD SPLIT+BAT SPEED
10 YARD SPLIT+BALL SPEED/VELOCITY
10 YARD SPLIT+DISTANCE
10 YARD SPLIT+BARREL ACCURACY
10 YARD SPLIT+BARREL ANGLE
10 YARD SPLIT+GLOVE TO RELEASE
10 YARD SPLIT+RANGE
10 YARD SPLIT+THROWING ACCURACY
VERTICAL JUMP+BROAD JUMP
VERTICAL JUMP+RANGE
BROAD JUMP+RANGE
60 YARD+ARM STRENGTH+BAT SPEED
60 YARD+ARM STRENGTH+DISTANCE
60 YARD+ARM STRENGTH+BALL SPEED/VELOCITY
60 YARD+ARM STRENGTH+BARREL ACCURACY
60 YARD+ARM STRENGTH+GLOVE TO RELEASE
60 YARD+ARM STRENGTH+THROWING ACCURACY
60 YARD+ARM STRENGTH+RANGE
60 YARD+ARM STRENGTH+BARREL ANGLE
60 YARD+BAT SPEED+DISTANCE
60 YARD+BAT SPEED+BALL SPEED/VELOCITY
60 YARD+BAT SPEED+BARREL ACCURACY
60 YARD+BAT SPEED+BARREL ANGLE
60 YARD+BAT SPEED+RANGE
60 YARD+BAT SPEED+GLOVE TO RELEASE
60 YARD+BAT SPEED+THROWING ACCURACY
60 YARD+BALL SPEED/VELOCITY+BARREL ANGLE
60 YARD+BALL SPEED/VELOCITY+RANGE
60 YARD+BALL SPEED/VELOCITY+THROWING ACCURACY
60 YARD+BALL SPEED/VELOCITY+GLOVE TO RELEASE
60 YARD+BALL SPEED/VELOCITY+BARREL ACCURACY
60 YARD+BALL SPEED/VELOCITY+DISTANCE
60 YARD+GLOVE TO RELEASE+DISTANCE
60 YARD+GLOVE TO RELEASE+BARREL ACCURACY
60 YARD+GLOVE TO RELEASE+BARREL ANGLE
60 YARD+GLOVE TO RELEASE+THROWING ACCURACY
60 YARD+GLOVE TO RELEASE+RANGE
60 YARD+GLOVE TO RELEASE+DISTANCE
60 YARD+DISTANCE+BARREL ACCURACY
60 YARD+DISTANCE+BARREL ANGLE
60 YARD+DISTANCE+RANGE
60 YARD+DISTANCE+THROWING ACCURACY
60 YARD+BARREL ACCURACY+BARREL ANGLE
60 YARD+BARREL ACCURACY+RANGE
60 YARD+BARREL ACCURACY+THROWING ACCURACY
60 YARD+BARREL ANGLE+RANGE
60 YARD+BARREL ANGLE+THROWING ACCURACY

Football Athletic Ability:

As discussed above, the present invention may be used to assess athletic ability in a variety of activities. Although some of the above mentioned embodiments are directed to baseball, the present invention is not limited in this respect. For example, FIGS. 10A-10E illustrates representative performance scores for a plurality of football athletic parameters. As shown in FIGS. 10A-10E, in one embodiment, example performance scores are provided for different football positions, such as quarterback, running back, full back, and wide receiver, because different characteristics determine athletic ability for these different positions. The following table provides an exemplary list of football athletic parameters, some of which are illustrated in FIGS. 10A-10E.

| Football Athletic Parameters | |
|---|---|
| Athletic Parameter | Description |
| 40 Yard Dash | A 40 yard sprint, measured in seconds. |
| 60 Yard Dash | A 60 yard sprint, measured in seconds. |
| 10 Yard Split/Acceleration | A 10 yard sprint that is measured in seconds from a stopped position to a full stride. |
| 20 Yard Shuttle | The 20 Yard Shuttle is a short sprint to gauge agility, starting 5 yards to the left, 10 yards to the right, then 5 yards to the left. |
| 60 Yard Shuttle | The 60 Yard Shuttle is a short sprint to gauge agility, starting 15 yards to the left, 30 yards to the right, then 15 yards to the left. |
| 3, 5 or 7 Step Drop Time | This is a timed measurement in seconds of a quarterback's footwork as he moves back and gets set to pass from a set position under center. |
| Release Time | Release time is the amount of time the quarterback has the ball from a set position to release of the ball. (Similar to "Separation to Release" discussed above) |
| Compression Force Rate Drive | This is a timed measurement of how fast a player can hit and move a 300 lb. blocking sled for a length of 5-10 yards. |
| Bench Press | This is a measure of how much the player is able to bench press (number of reps of a certain weight - may be 185 lbs for high school athletes and 225 lbs for college athletes). |
| Vertical Jump | This is a measure of jumping ability, measured in vertical feet or inches. |

-continued

Football Athletic Parameters

| Athletic Parameter | Description |
|---|---|
| Broad Jump | This is a measure of jumping ability, measured in horizontal feet. |
| Arm Speed | This is a measure of a quarterback's arm speed while throwing a football, measured in MPH. |
| Throwing Accuracy | Throwing accuracy is equal to the percentage that the quarterback throws a ball that hits a particular target. |
| Height | A Player's height, typically in feet, inches |
| Weight | A Player's weight, typically in pounds |
| Wonderlic Score | This is a player's score on the Wonderlic Personnel Test, an intelligence test, which is primarily used for prospective players in the National Football League (NFL). |

FIGS. 10A-10E provide representative combinations for predicting athletic ability of a football player. It should be recognized that other combinations of athletic parameters may be used to determine athletic ability, as the present invention is not limited in this respect. Additional exemplary combinations of athletic parameters which may be used to predict athletic ability of a football player are provided in the following list.

Additional Football Combinations

BENCH PRESS+40 YARD
BENCH PRESS+20 YARD SHUTTLE
BENCH PRESS+HEIGHT/WEIGHT
BENCH PRESS+60 YARD
BENCH PRESS+60 YARD LONG SHUTTLE
BENCH PRESS+BROAD JUMP
BENCH PRESS+VERTICAL JUMP
BENCH PRESS+COMPRESSION FORCE RATE
BENCH PRESS+COMPRESSION FORCE DRIVE
BENCH PRESS+10 YARD SPLIT
BENCH PRESS+WONDERLIC TEST
40 YARD+20 YARD SHUTTLE
40 YARD+HEIGHT/WEIGHT
40 YARD+60 YARD
40 YARD+60 YARD SHUTTLE
40 YARD+BROAD JUMP
40 YARD+VERTICAL JUMP
40 YARD+COMPRESSION FORCE RATE
40 YARD+COMPRESSION FORCE DRIVE
40 YARD+10 YARD SPLIT
40 YARD+WONDERLIC TEST
20 YARD SHUTTLE+HEIGHT/WEIGHT
20 YARD SHUTTLE+60 YARD
20 YARD SHUTTLE+60 YARD SHUTTLE
20 YARD SHUTTLE+BROAD JUMP
20 YARD SHUTTLE+VERTICAL JUMP
20 YARD SHUTTLE+COMPRESSION FORCE RATE
20 YARD SHUTTLE+COMPRESSION FORCE DRIVE
20 YARD SHUTTLE+10 YARD SPLIT
20 YARD SHUTTLE+WONDERLIC TEST
HEIGHT/WEIGHT+60 YARD
HEIGHT/WEIGHT+60 YARD LS
HEIGHT/WEIGHT+BROAD JUMP
HEIGHT/WEIGHT+VERTICAL JUMP
HEIGHT/WEIGHT+COMPRESSION FORCE RATE
HEIGHT/WEIGHT+COMPRESSION FORCE DRIVE
HEIGHT/WEIGHT+10 YARD SPLIT
60 YARD+60 YARD SHUTTLE
60 YARD+BROAD JUMP
60 YARD+VERTICAL JUMP
60 YARD+COMPRESSION FORCE RATE
60 YARD+COMPRESSION FORCE DRIVE
60 YARD+10 YARD SPLIT
60 YARD+WONDERLIC TEST
60 YARD LONG SHUTTLE+3 CONE DRILL
60 YARD SHUTTLE+BROAD JUMP
60 YARD SHUTTLE+VERTICAL JUMP
60 YARD SHUTTLE+COMPRESSION FORCE RATE
60 YARD SHUTTLE+COMPRESSION FORCE DRIVE
60 YARD SHUTTLE+10 YARD SPLIT
60 YARD SHUTTLE+WONDERLIC TEST
BROAD JUMP+VERTICAL JUMP
BROAD JUMP+COMPRESSION FORCE RATE
BROAD JUMP+COMPRESSION FORCE DRIVE
BROAD JUMP+10 YARD SPLIT
BROAD JUMP+WONDERLIC TEST
VERTICAL JUMP+COMPRESSION FORCE RATE
VERTICAL JUMP+COMPRESSION FORCE DRIVE
VERTICAL JUMP+10 YARD SPLIT
VERTICAL JUMP+WONDERLIC TEST
COMPRESSION FORCE RATE+COMPRESSION FORCE DRIVE
COMPRESSION FORCE RATE+10 YARD SPLIT
COMPRESSION FORCE RATE+WONDERLIC TEST
COMPRESSION FORCE DRIVE+10 YARD SPLIT
COMPRESSION FORCE DRIVE+WONDERLIC TEST
10 YARD SPLIT+WONDERLIC TEST

Aspects of the present invention are directed to a system for predicting athletic ability, where the system includes at least one device for measuring at least a first athletic parameter and a second athletic parameter that is different from the first athletic parameter. As discussed above, a variety of devices may be used to measure the athletic parameters. In one embodiment, a time measuring device is provided to measure an athletic parameter. The time measuring device may be used to measure a player's performance in a 40 or 60 yard dash, or a 20 or 60 yard shuttle. A timing device may also be used to measure a player's acceleration, or the glove to release time of a catcher or fielder.

In one embodiment, a radar device is used to measure an athletic parameter such as ball speed, bat speed, or ball movement. For example, the device to measure an athletic parameter may include a radar gun which includes a radio transmitter and receiver.

In one particular embodiment, a Doppler radar device is used to measure at least one athletic parameter. A Doppler radar device uses a phenomenon known as the Doppler Effect (the change in apparent frequency of a radio wave as an observer and the source of the radio wave moves toward or away from each other) to measure the speed of an object. In one embodiment, a Doppler radar device may be used to determine the three-dimensional movement of an object, such as a ball. The Doppler radar device may be used to obtain data relating to the speed, spin and/or trajectory of an object. The device for measuring an athletic parameter may continuously transmit radio signals that experience a change in frequency when they bounce off a moving object. This change in frequency may be translated into a velocity of the object. In one embodiment, a device for measuring an athletic parameter may include a phased array Doppler radar, which includes at least one radar transmitter and a plurality of receivers. A device with a plurality of receivers may be able to measure the three-dimensional position of a portion of, or the entire trajectory of an object. In one particular embodiment, a device used to measure an athletic parameter is a Doppler radar device sold under the name Trackman™, manufactured by ISG A/S located in Brighton, Mich.

In other embodiments, a video imager is provided to measure an athletic parameter. The video imager may be used to measure parameters such as stride length, arm angle, distance to release, and stride length.

In yet other embodiments, a pressure sensor is provided to measure an athletic parameter. A pressure sensor may be used to measure parameters such as a hitter's weight distribution and throwing accuracy. Other devices which include ultrasonic technology, motion sensors, video and/or still cameras, light gate triggers, target sensors, machine vision, and other computer-controlled devices may also be used according to aspects of the present invention.

In one embodiment, the system for predicting athletic ability may be portable such that a coach or scout can easily take it to a game, arena, or practice facility. In one embodiment, the system, or at least a portion of the system, is hand-held. In other embodiments, the system for predicting athletic ability may be built into various facilities such as arenas, ballparks and/or batting cages. It should be appreciated that in some embodiments, a device for measuring an athletic parameter may communicate remotely with a computer which calculates the performance score. In some embodiments, electrical wires connect a device with a computer, whereas in other embodiments, the components may wirelessly connect with each other to transmit athletic parameters information.

It should be appreciated that various embodiments of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A method for predicting athletic ability, the method comprising:
    measuring a first athletic parameter with a first device at a first area in response to a first stimulus;
    measuring a second athletic parameter with a second device at a second area distinct from the first area in response to a second stimulus, wherein the second athletic parameter is different from the first athletic parameter;
    calculating a performance score using a computer based upon the first athletic parameter and the second athletic parameter, wherein the performance score is predictive of athletic ability scaling the performance score based on each measured athletic parameter to a scouting scale; and
    creating a scouting report based on the scaled performance score.

2. The method of claim 1, further comprising:
    measuring a third athletic parameter; and
    wherein calculating a performance score is based upon the first athletic parameter, the second athletic parameter and the third athletic parameter.

3. The method of claim 2, wherein the performance score is predictive of the baseball hitting athletic ability, wherein the first parameter is a speed of a bat swung by a batter, the second parameter is a speed of a ball after the ball is hit with the bat by the batter, and the third parameter is a distance the ball travels after the ball is hit by the batter.

4. The method of claim 1, wherein the first athletic parameter is directed to movement of an athlete.

5. The method of claim 4, wherein the first athletic parameter is a distance.

6. The method of claim 4, wherein the first athletic parameter is an angle of rotation.

7. The method of claim 4, wherein the first athletic parameter is a velocity.

8. The method of claim 4, wherein the first athletic parameter is a time period.

9. The method of claim 1, wherein the first athletic parameter is directed to movement of an object by an athlete.

10. The method of claim 9, wherein the first athletic parameter is a distance.

11. The method of claim 9, wherein the first athletic parameter is an angle of rotation.

12. The method of claim 9, wherein the first athletic parameter is a velocity.

13. The method of claim 9, wherein the first athletic parameter is a time period.

14. The method of claim 1, wherein calculating a performance score includes weighing the first athletic parameter more than the second athletic parameter, such that the resulting performance score is affected more by the measurement of the first athletic parameter than the measurement of the second athletic parameter.

15. The method of claim 1, wherein a first value is obtained when measuring a first athletic parameter, a second value is obtained when measuring a second athletic parameter, and wherein calculating a performance score includes inputting the first and second values into a formula to generate the performance score.

16. The method of claim 15, wherein calculating a performance score includes weighing the first value more than the second value in the formula, such that the resulting performance score is affected more by the measurement of the first athletic parameter than the measurement of the second athletic parameter.

17. The method of claim 15, further comprising:
    selecting the formula for generating the performance score based upon at least the first and second athletic parameters.

18. The method of claim 1, further comprising storing the performance score into a database.

19. The method of claim 18, further comprising storing a plurality of performance scores for an athlete over a period of time which is representative of the change in athletic ability.

20. The method of claim 18, further comprising storing a plurality of performance scores for a plurality of athletes to create a scouting report.

21. The method of claim 1, wherein the performance score is predictive of the baseball pitching athletic ability, wherein the first parameter is a speed of the ball thrown by a baseball pitcher during a pitch, and the second parameter is movement of the ball thrown during the pitch, wherein the movement of the ball during the pitch includes horizontal movement and vertical movement of the ball measured at a location proximate home plate.

* * * * *